US012699103B2

(12) United States Patent
Kurt Celep et al.

(10) Patent No.: US 12,699,103 B2
(45) Date of Patent: Aug. 4, 2026

(54) BIOLOGICAL MARKERS IN THE DIAGNOSIS OF ENDOMETRIOSIS

(71) Applicant: YEDITEPE UNIVERSITESI, Istanbul (TR)

(72) Inventors: Inci Kurt Celep, Istanbul (TR); Dilek Telci Temeltas, Istanbul (TR); Fikrettin Sahin, Istanbul (TR); Melike Batukan, Istanbul (TR); Halime Siginc, Istanbul (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 365 days.

(21) Appl. No.: 18/562,841

(22) PCT Filed: May 20, 2022

(86) PCT No.: PCT/TR2022/050458
§ 371 (c)(1),
(2) Date: Nov. 21, 2023

(87) PCT Pub. No.: WO2022/245324
PCT Pub. Date: Nov. 24, 2022

(65) Prior Publication Data
US 2024/0241134 A1     Jul. 18, 2024

(30) Foreign Application Priority Data
May 21, 2021    (TR) ............................... 2021/008431

(51) Int. Cl.
*G01N 33/573* (2006.01)
*G01N 33/68* (2006.01)

(52) U.S. Cl.
CPC ......... *G01N 33/689* (2013.01); *G01N 33/573* (2013.01); *G01N 2333/49* (2013.01); *G01N 2333/70596* (2013.01); *G01N 2333/91085* (2013.01); *G01N 2800/364* (2013.01); *G01N 2800/52* (2013.01)

(58) Field of Classification Search
None
See application file for complete search history.

(56) References Cited

U.S. PATENT DOCUMENTS

2014/0364341 A1* 12/2014 Mansfield .......... G01N 33/6893
506/18

OTHER PUBLICATIONS

Dilek Telci, et al., Tissue transglutaminase (TG2)—a wound response enzyme, Frontiers in Bioscience, 2006, pp. 867-882, vol. 11.
Maria V. Nurminskaya, et al., Cellular Functions of Tissue Transglutaminase, International Review of Cell and Molecular Biology, 2012, pp. 1-97, vol. 294.

Elisabetta A. M. Verderio, et al., A Novel RGD-independent Cell Adhesion Pathway Mediated by Fibronectin-bound Tissue Transglutaminase Rescues Cells from Anoikis, The Journal of Biological Chemistry, 2003, pp. 42604-42614, vol. 278, No. 43.
Jansina Y. Fok, et al., Implications of tissue transglutaminase expression in malignant melanoma, Mol Cancer Ther, 2006, pp. 1493-1503, vol. 5, No. 6.
Jansina Y. Fok, et al., Tissue transglutaminase induces the release of apoptosis inducing factor and results in apoptotic death of pancreatic cancer cells, Apoptosis, 2007, pp. 1455-1463, vol. 12.
JF Herman, et al., Implications of increased tissue transglutaminase (TG2) expression in drug-resistant breast cancer (MCF-7) cells, Oncogene, 2006, pp. 3049-3058, vol. 25.
Amit Verma, et al., Increased Expression of Tissue Transglutaminase in Pancreatic Ductal Adenocarcinoma and Its Implications in Drug Resistance and Metastasis, Cancer Research, 2006, pp. 10525-10533, vol. 66, No. 21.
Merve Erdem, et al., Up-regulation of TGM2 with ITGB1 and SDC4 is important in the development and metastasis of renal cell carcinoma, Urologic Oncology: Seminars and Original Investigations, 2013, pp. 1-8.
Selcuk Erdem, et al., The increased transglutaminase 2 expression levels during initial tumorigenesis predict increased risk of metastasis and decreased disease-free and cancer-specific survivals in renal cell carcinoma, World J. Urol, 2015, pp. 1553-1560, vol. 33.
Kapil Mehta, Tissue transglutaminase expression and drug resistance in ovarian cancer, Expert Review of Obstetrics & Gynecology, 2009, pp. 105-110, 4(2).
Jurgen M. Lehmann, et al., Discrimination between Benign and Malignant Cells of Melanocytic Lineage by Two Novel Antigens, a Glycoprotein with a Molecular Weight of 113,000 and a Protein with a Molecular Weight of 76,000, Cancer Research, 1987, pp. 841-845, vol. 47.
Allal Ouhtit, et al., Towards understanding the mode of action of the multifaceted cell adhesion receptor CD146, Biochimica et Biophysica Acta, 2009, pp. 130-136, vol. 1795.
Jean-Christophe Noel, et al., Lymph node involvement and lymphovascular invasion in deep infiltrating rectosigmoid endometriosis, Fertility and Sterility, 2008, pp. 1069-1072, vol. 89, No. 5.
Shinji Ogawa, et al., Ovarian Endometriosis Associated with Ovarian Carcinoma: A Clinicopathological and Immunohistochemical Study, Gynecologic Oncology, 2000, pp. 298-304, vol. 77.
Susan C. Modesitt, et al., Ovarian and Extraovarian Endometriosis-Associated Cancer, The American College of Obstetricians and Gynecologists, 2002, pp. 788-795, vol. 100, No. 4.
Lisbeth Bertelsen, et al., Risk for breast cancer among women with endometriosis, Int. J. Cancer, 2007, pp. 1372-1375, vol. 120.

(Continued)

*Primary Examiner* — Michelle F. Paguio Frising
(74) *Attorney, Agent, or Firm* — Bayramoglu Law Offices LLC

(57) ABSTRACT

Combinations of the novel biological markers that can be used in the diagnosis of endometriosis are provided. The objective of the invention is to detect biological markers that are expressed differently in eMSCs isolated from endometrial biopsy samples in the diagnosis of endometriosis compared to healthy eMSCs. A tissue transglutaminase is configured as a biomarker for a diagnosis of an endometriosis in isolated endometrial mesenchymal stem cells derived from an endometrial biopsy and/or a menstrual blood from endometriosis patients.

10 Claims, 17 Drawing Sheets

(56)　　　　　　References Cited

OTHER PUBLICATIONS

Yuan Wang, et al., Over-Expression of Platelet-Derived Growth Factor-D Promotes Tumor Growth and Invasion in Endometrial Cancer, International Journal of Molecular Sciences, 2014, pp. 4780-4794, vol. 15.

Linda Fredriksson, et al., The PDGF family: four gene products form five dimeric isoforms, Cytokine & Growth Factor Reviews, 2004, pp. 197-204, vol. 15.

Jiuhong Yu, et al., Platelet-derived Growth Factor Signaling and Human Cancer, Journal of Biochemistry and Molecular Biology, 2003, pp. 49-59, vol. 36, No. 1.

Zhiwei Wang, et al., PDGF-D Signaling: A Novel Target in Cancer Therapy, Current Drug Targets, 2009, pp. 38-41, vol. 10, No. 1.

Caroline E. Gargett, et al., Endometrial stem/progenitor cells: the first 10 years, Human Reproduction Update, 2015, pp. 1-27, vol. 0, No. 0.

Caroline E. Gargett, et al., Endometrial Mesenchymal Stem/Stromal Cells, Their Fibroblast Progeny in Endometriosis, and More, Biology of Reproduction, 2016, pp. 1-4, vol. 94, No. 6.

Fatima Barragan, et al., Human Endometrial Fibroblasts Derived from Mesenchymal Progenitors Inherit Progesterone Resistance and Acquire an Inflammatory Phenotype in the Endometrial Niche in Endometriosis, Biology of Reproduction, 2016, pp. 1-20, vol. 94, No. 5.

Ayse Hande Nayman, et al., Dual-Inhibition of mTOR and Bcl-2 Enhances the Anti-tumor Effect of Everolimus against Renal Cell Carcinoma In Vitro and In Vivo, Journal of Cancer, 2019, pp. 1466-1478, vol. 10, No. 6.

Alexander V. Peskin, et al., A microtiter plate assay for superoxide dismutase using a water-soluble tetrazolium salt (WST-1), Clinica Chimica Acta, 2000, pp. 157-166, vol. 293.

Elham N. Samani, et al., Micrometastasis of endometriosis to distant organs in a murine model, Oncotarget, 2019, pp. 2282-2291, vol. 10, No. 23.

Xin Gao, et al., Economic burden of endometriosis, Fertility and Sterility, 2006, pp. 1561-1572, vol. 86, No. 6.

Vineet V. Mishra, et al., Prevalence; Characteristics and Management of Endometriosis Amongst Infertile Women: A One Year Retrospective Study, Journal of Clinical and Diagnostic Research, 2015, pp. 1-3, vol. 9, No. 6.

VH Eisenberg, et al., Epidemiology of endometriosis: a large population-based database study from a healthcare provider with 2 million members, BJOG an International Journal of Obstetrics and Gynaecology, 2018, pp. 55-62, vol. 125.

Ahmed M. Soliman, et al., Real-World Evaluation of Direct and Indirect Economic Burden Among Endometriosis Patients in the United States, Advances in Therapy, 2018, pp. 408-423, vol. 35.

Peng-Hui Wang, et al., Major Complications of Operative and Diagnostic Laparoscopy for Gynecologic Disease, The Journal of the American Association of Gynecologic Laparoscopists, 2001, pp. 68-73, vol. 8, No. 1.

Adi Y Weintraub, et al., Think Endometriosis: Delay in Diagnosis or Delay in Referral to Adequate Treatment?, Journal of Fertilization: In Vitro, IVF-Worldwide, Reproductive Medicine, Genetics & Stem Cell Biology, 2014, vol. 2, Issue 3.

Martin Hirsch, et al., Preoperative assessment and diagnosis of endometriosis: are we any closer?, Current Opinion in Obstetrics and Gynecology, 2015, pp. 284-290, vol. 27, No. 4.

Rachel W.S. Chan, et al., Clonogenicity of Human Endometrial Epithelial and Stromal Cells, Biology of Reproduction, 2004, pp. 1738-1750, vol. 70.

M Dominici, et al., Minimal criteria for defining multipotent mesenchymal stromal cells. The International Society for Cellular Therapy position statement, Cytotherapy, 2006, pp. 315-317, vol. 8, No. 4.

Xiaolong Meng, et al., Endometrial regenerative cells: A novel stem cell population, Journal of Translational Medicine, 2007, pp. 1-10, vol. 5, No. 57.

Hirotaka Masuda, et al., Endometrial Side Population Cells: Potential Adult Stem/Progenitor Cells in Endometrium, Biology of Reproduction, 2015, pp. 1-8, vol. 93, No. 4.

Caroline E. Gargett, Identification and characterisation of human endometrial stem/progenitor cells, Australian and New Zealand Journal of Obstetrics and Gynaecology, 2006, pp. 250-253, vol. 46.

Caroline E. Gargett, Endometrial reconstruction from stem cells, Fertility and Sterility, 2012, pp. 11-20, vol. 98, No. 1.

K.E. Schwab, et al., Co-expression of two perivascular cell markers isolates mesenchymal stem-like cells from human endometrium, Human Reproduction, 2007, pp. 2903-2911, vol. 22, No. 11.

Evgeny A. Zemskov, et al., Regulation of Platelet-derived Growth Factor Receptor Function by Integrin-associated Cell Surface Transglutaminase, The Journal of Biological Chemistry, 2009, pp. 16693-16703, vol. 284, No. 24.

Evgeny A. Zemskov, et al., Tissue Transglutaminase Promotes PDGF/PDGFR-Mediated Signaling and Responses in Vascular Smooth Muscle Cells, Journal of Cellular Physiology, 2012, pp. 2089-2096, vol. 227.

Jianan Chen, et al., CD146 is essential for PDGFRB-induced pericyte recruitment, Protein Cell, 2018, pp. 743-747, vol. 9, No. 8.

Chris B. Moore, et al., Short Hairpin RNA (shRNA): Design, Delivery, and Assessment of Gene Knockdown, RNA Therapeutics, Methods in Molecular Biology, 2010, pp. 139-156, vol. 629.

J.E. Folk, et al., Mechanism and Basis for Specificity of Transglutaminase-Catalyzed ε-(γ-Glutamyl) lysine Bond Formation, Advances of Enzymology and Related Areas of Molecular Biology, 1983, pp. 1-56. vol. 54.

Pierre De Macedo, et al., A Direct Continuous Spectrophotometric Assay for Transglutaminase Activity, Analytical Biochemistry, 2000, pp. 16-20, vol. 285.

Siiri E. Iismaa, et al., Transglutaminases and Disease: Lessons From Genetically Engineered Mouse Models and Inherited Disorders, Physiol Rev, 2009, pp. 991-1023, vol. 89.

Inci Kurt Celep, Tissue Transglutaminase as a Novel Therapeutic Biomarker in the Development of Endometriosis, Yeditepe University Submitted to Graduate School of Natural and Applied Sciences in Partial Fulfillment of the Requirements for the Degree of Doctor of Philosophy in Biotechnology, 2019, pp. 1-272.

John A. Sampson, et al., Peritoneal Endometriosis Due to the Menstrual Dissemination of Endometrial Tissue into the Peritoneal Cavity, Transactions of the Fifty-second Annual Meeting of the American Gynecological Society, 1927, pp. 422-469.

Daniel W. Cramer, et al., The Epidemiology of Endometriosis, Annals New York Academy of Sciences, pp. 11-22, (2002).

Gretchen E. Tietjen, et al., Endometriosis Is Associated with Prevalence of Comorbid Conditions in Migraine, Headache, 2007, pp. 1069-1078, vol. 47.

Sandra G. Pasoto, et al., Endometriosis and Systemic Lupus Erythematosus: A Comparative Evaluation of Clinical Manifestations and Serological Autoimmune Phenomena, American Journal of Reproductive Immunology, 2005, pp. 85-93, vol. 53.

N. Sinaii, et al., High rates of autoimmune and endocrine disorders, fibromyalgia, chronic fatigue syndrome and atopic diseases among women with endometriosis: a survey analysis, Human Reproduction, 2002, pp. 2715-2724, vol. 17, No. 10.

Karen Lamb, et al., Endometriosis: A Comparison of Associated Disease Histories, American Journal of Preventive Medicine, 1986, pp. 324-329, vol. 2, No. 6.

Alexandra J. Mao, et al., Diagnosis and management of endometriosis: The role of the advanced practice nurse in primary care, Journal of the American Academy of Nurse Practitioners, 2010, pp. 109-116, vol. 22.

Edgardo Somigliana, et al., Non-invasive diagnosis of endometriosis: the goal or own goal?, Human Reproduction, 2010, pp. 1863-1868, vol. 25, No. 8.

Sachiko Matsuzaki, et al., Analysis of risk factors for the removal of normal ovarian tissue during laparoscopic cystectomy for ovarian endometriosis, Human Reproduction, 2009, pp. 1402-1406, vol. 24, No. 6.

Austin Zanelotti, et al., Surgery and Endometriosis, Clin Obstet Gynecol, 2017, pp. 477-484, vol. 60, No. 3.

(56) References Cited

OTHER PUBLICATIONS

Jo Kitawaki, et al., Usefulness and limits of CA-125 in diagnosis of endometriosis without associated ovarian endometriomas, Human Reproduction, 2005, pp. 1999-2003, vol. 20, No. 7.

Brenda Eskenazi, et al., Epidemiology of Endometriosis, Obstetrics and Gynecology Clinics of North America, 1997, pp. 235-258, vol. 24, No. 2.

Paolo Vercellini, et al., Endometriosis: pathogenesis and treatment, Nature Reviews Endocrinology, 2014, pp. 261-275, vol. 10.

John A. Sampson, Ovarian Hematomas of Endometrial Type (Perforating Hemorrhagic Cysts of the Ovary) and Implantation Adenomas of Endometrial Type, The Boston Medical and Surgical Journal, 1922, pp. 445-456, vol. 186, No. 14.

Mario Vignali, et al., Endometriosis: novel etiopathogenetic concepts and clinical perspectives., Fertility and Sterility, 2002, pp. 665-678, vol. 78, No. 4.

D. Vinatier, et al., Immunological aspects of endometriosis, Human Reproduction, 1996, pp. 371-384, vol. 2, No. 5.

Giuseppe Matarese, et al., Pathogenesis of endometriosis: natural immunity dysfunction or autoimmune disease?, Trends in Molecular Medicine, 2003, pp. 223-228, vol. 9, No. 5.

Cleophas M Kyama, et al., Potential involvement of the immune system in the development of endometriosis, Reproductive Biology and Endocrinology, 2003, pp. 1-9, 1:123.

B.F. Barrier, et al., HLA-G is expressed by the glandular epithelium of peritoneal endometriosis but not in eutopic endometrium, Human Reproduction, 2006, pp. 864-869, vol. 21, No. 4.

Edgardo Somigliana, et al., Bladder endometriosis: getting closer and closer to the unifying metastatic hypothesis, Fertility and Sterility, 2007, pp. 1287-1290, vol. 87, No. 6.

Wen Di, et al., The search for genetic variants predisposing women to endometriosis, Current Opinion in Obstetrics and Gynecology, 2007, pp. 395-401, vol. 19.

K. Kashima, et al., Familial risk among Japanese patients with endometriosis, International Journal of Gynecology and Obstetrics, 2004, pp. 61-64, vol. 84.

Sherry Rier, et al., Environmental Dioxins and Endometriosis, Toxicological Sciences, 2002, pp. 161-170, vol. 70.

Francis S. Collins, et al., Implications of the Human Genome Project for Medical Science, JAMA, 2001, pp. 540-544, vol. 285, No. 5.

Steven D. Kleeman, et al., Gynecologic Anatomy, General Gynecology: The Requisites in Obstetrics and Gynecology, Chapter 4; Elsevier Health Sciences (2007), pp. 73-98.

A. Starzinski-Powitz, et al., In Search of Pathogenic Mechanisms in Endometriosis: The Challenge for Molecular Cell Biology, Current Molecular Medicine, 2001, pp. 655-664, vol. 1.

C.E. Gargett, Uterine stem cells: What is the evidence?, Human Reproduction Update, 2007, pp. 87-101, vol. 13, No. 1.

G. Leyendecker, et al., Endometriosis results from the dislocation of basal endometrium, Human Reproduction, 2002, pp. 2725-2736, vol. 17, No. 10.

Isaac E. Sasson, et al., Stem Cells and the Pathogenesis of Endometriosis, Ann N Y Acad Sci., 2008, pp. 106-115, vol. 1127.

Asgerally T. Fazleabas, et al., A Modified Baboon Model for Endometriosis, Annals New York Academy of Sciences, pp. 308-317, (2002).

Sergey S. Akimov, et al., Tissue Transglutaminase Is an Integrin-binding Adhesion Coreceptor for Fibronectin, The Journal of Cell Biology, 2000, pp. 825-838, vol. 148, No. 4.

Claire A. Gaudry, et al., Cell Surface Localization of Tissue Transglutaminase Is Dependent on a Fibronectin-binding Site in Its N-terminal β-Sandwich Domain, The Journal of Biological Chemistry, 1999, pp. 30707-30714, vol. 274, No. 43.

Dilek Telci, et al., Fibronectin-Tissue Transglutaminase Matrix Rescues RGD-impaired Cell Adhesion through Syndecan-4 and β1 Integrin Co-signaling, The Journal of Biological Chemistry, 2008, pp. 20937-20947, vol. 283, No. 30.

Zhuo Wang, et al., RGD-independent Cell Adhesion via a Tissue Transglutaminase-Fibronectin Matrix Promotes Fibronectin Fibril Deposition and Requires Syndecan-½ and α5β1 Integrin Co-signaling, The Journal of Biological Chemistry, 2010, pp. 40212-40229, vol. 285, No. 51.

An-Pei Kao, et al., Comparative study of human eutopic and ectopic endometrial mesenchymal stem cells and the development of an in vivo endometriotic invasion model, Fertility and Sterility, 2011, pp. 1308-1315, vol. 95, No. 4.

Paola Vigano, et al., Endometriosis: epidemiology and aetiological factors, Best Practice & Research Clinical Obstetrics Gynaecology, 2004, pp. 177-200, vol. 18, No. 2.

Hirotaka Masuda, et al., A Novel Marker of Human Endometrial Mesenchymal Stem-Like Cells, Cell Transplantation, 2012, pp. 2201-2214, vol. 21.

I. Kurt, et al, Does tissue transglutaminase have a role in the development of endometriosis?, The Febs Journal, 2016, pp. 307-308, vol. 283.

Siiri E. Iismaa, et al., The Core Domain of the Tissue Transglutaminase Gh Hydrolyzes GTP and ATP, Biochemistry, 1997, pp. 11655-11664, vol. 36, No. 39.

Laszlo Lorand, et al., Transglutaminases: Crosslinking Enzymes With Pleiotropic Functions, Nature Reviews Molecular Cell Biology, 2003, pp. 140-156, vol. 4, Nature Publishing Group.

Nirmal K. Sarkar, et al., An enzymically catalyzed incorporation of amines into proteins, Biochimica et Biophysica Acta, 1957, pp. 451-452, vol. 25.

Eva Csosz, et al., Substrate Preference of Transglutaminase 2 Revealed by Logistic Regression Analysis and Intrinsic Disorder Examination, J. Mol. Biol., 2008, pp. 390-402, vol. 383.

Angelo Facchiano, et al., Transglutaminases and their substrates in biology and human diseases: 50 years of growing, Amino Acids, 2009, pp. 599-614, vol. 36.

Thung-S. Lai, et al., Role of tissue transglutaminase-2 (TG2)-mediated aminylation in biological processes, Amino Acids, 2016.

Charles S. Greenberg, et al., Transglutaminases: multifunctional cross-linking enzymes that stabilize tissues, The FASEB Journal, 1991, pp. 3071-3077, vol. 5.

Go Hasegawa, et al., A novel function of tissue-type transglutaminase: protein disulphide isomerase, Biochem. J., 2003, pp. 793-803, vol. 373.

Thung-Shenq Lai, et al., C-terminal Deletion of Human Tissue Transglutaminase Enhances Magnesium-dependent GTP/ATPase Activity, The Journal of Biological Chemistry, 1996, pp. 31191-31195, vol. 271, No. 49.

Raffaele Porta, et al, Mass Spectrometric Identification of the Amino Donor and Acceptor Sites in a Transglutaminase Protein Substrate Secreted from Rat Seminal Vesicles, Biochemistry, 1991, pp. 3114-3120, vol. 30, No. 12.

Alexey M. Belkin, Extracellular TG2: emerging functions and regulation, The FEBS Journal, 2011, pp. 4704-4716, vol. 278.

Martin Griffin, et al., Transglutaminases: Nature's biological glues, Biochem. J., 2002, pp. 377-396, vol. 368.

* cited by examiner

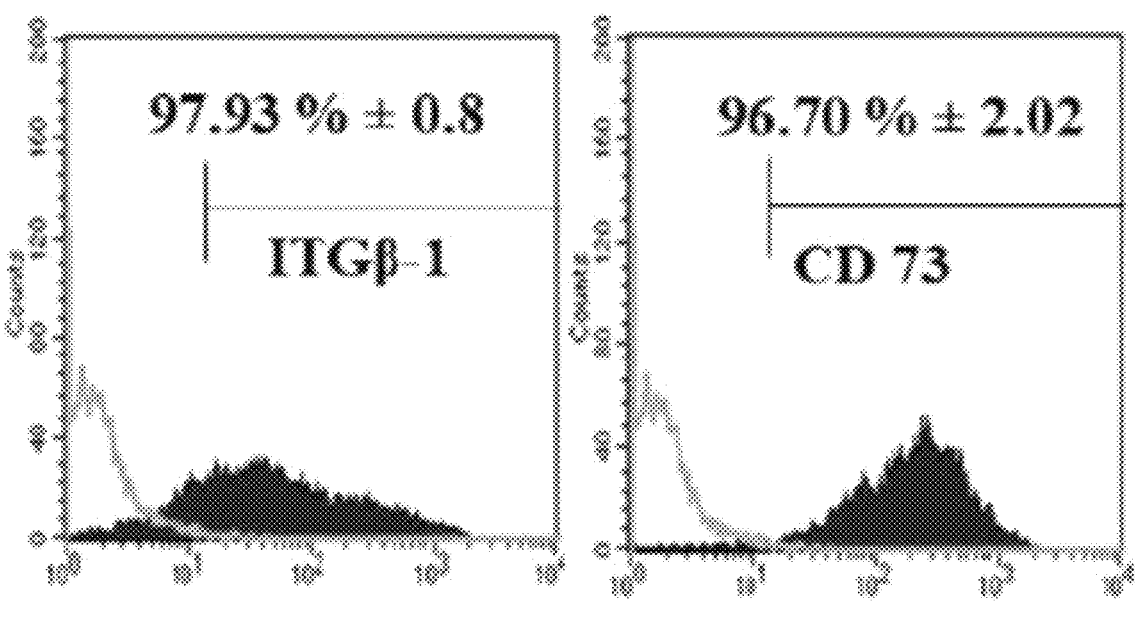
FIG. 2F                         FIG. 2G
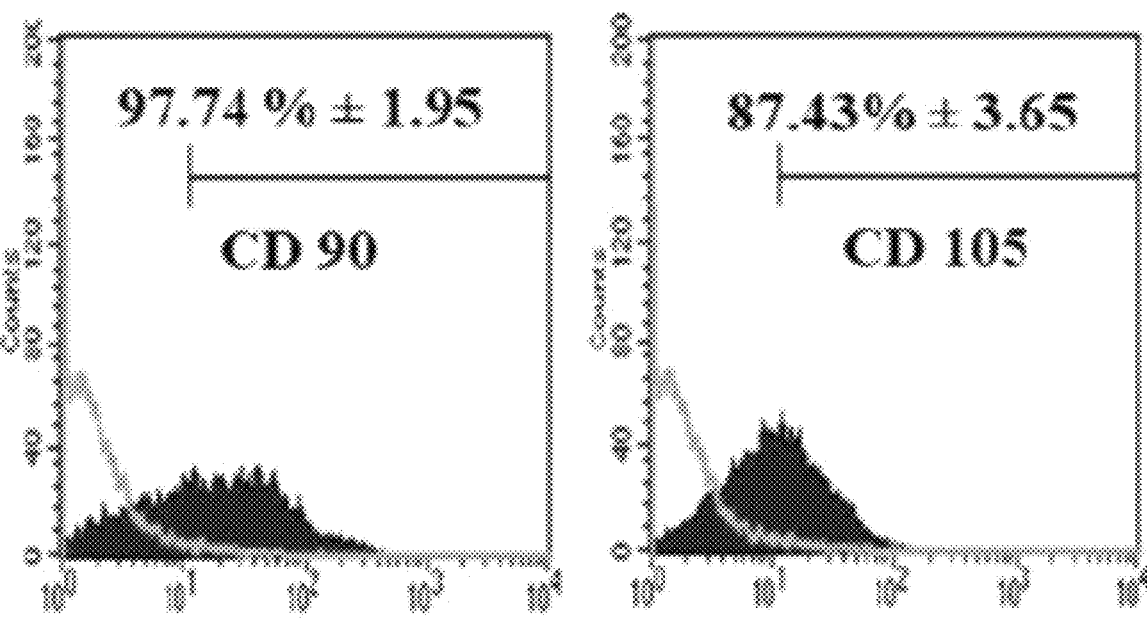
FIG. 2H                         FIG. 2I

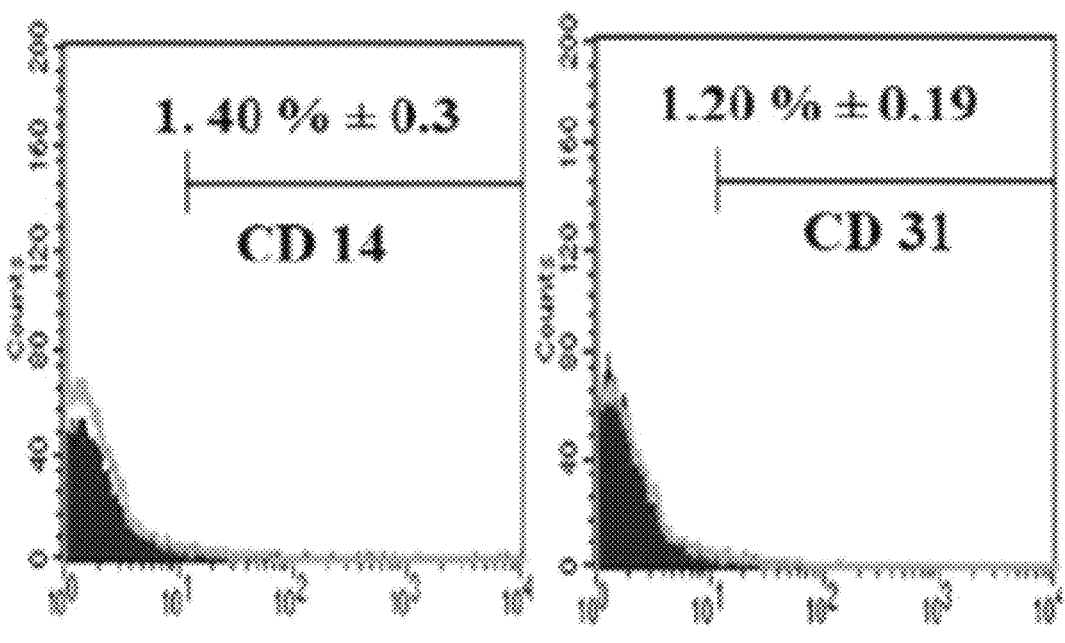
FIG. 2J                    FIG. 2K
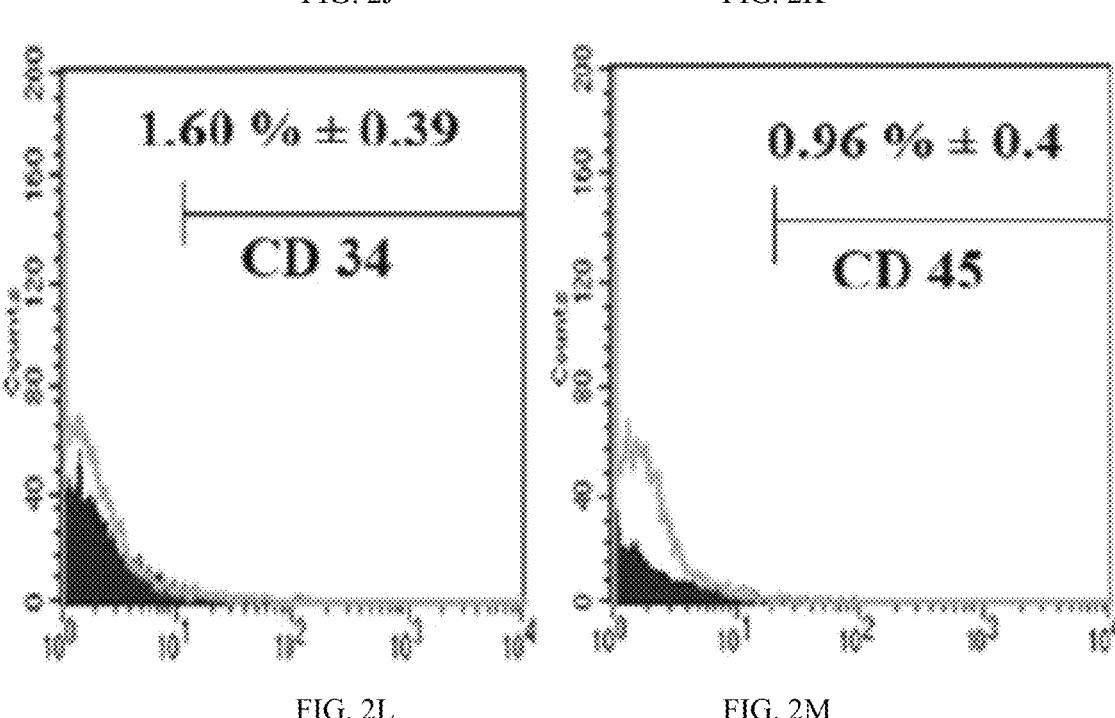
FIG. 2L                    FIG. 2M (a)
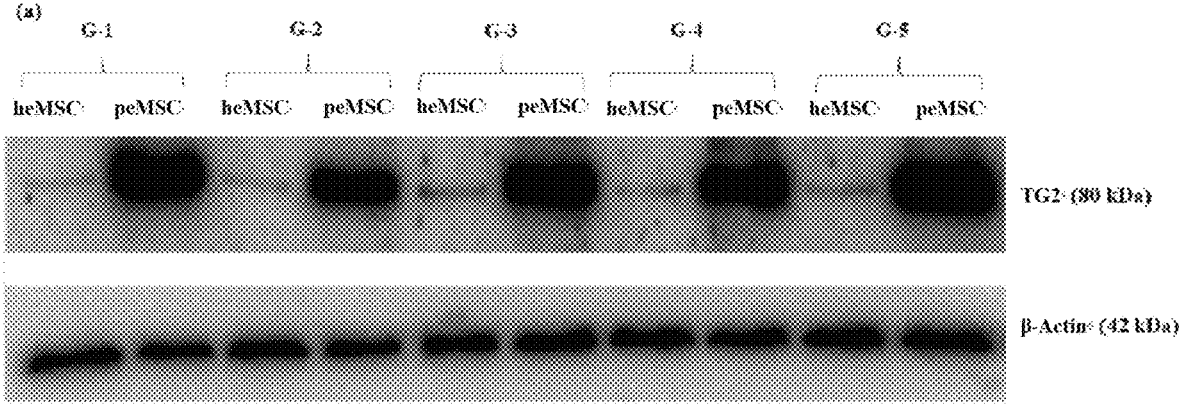
FIG. 3A
(b)
(c)
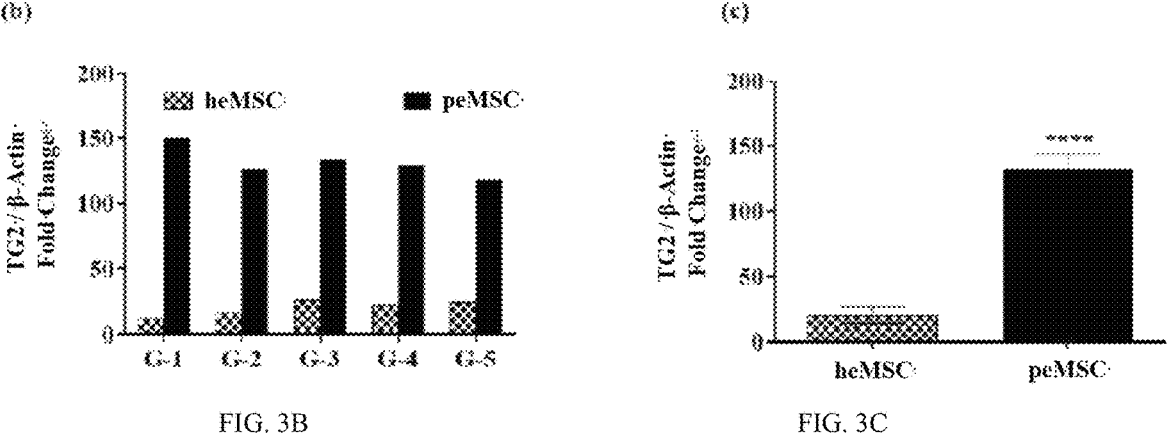
FIG. 3B
FIG. 3C (a)

(b)

(c)

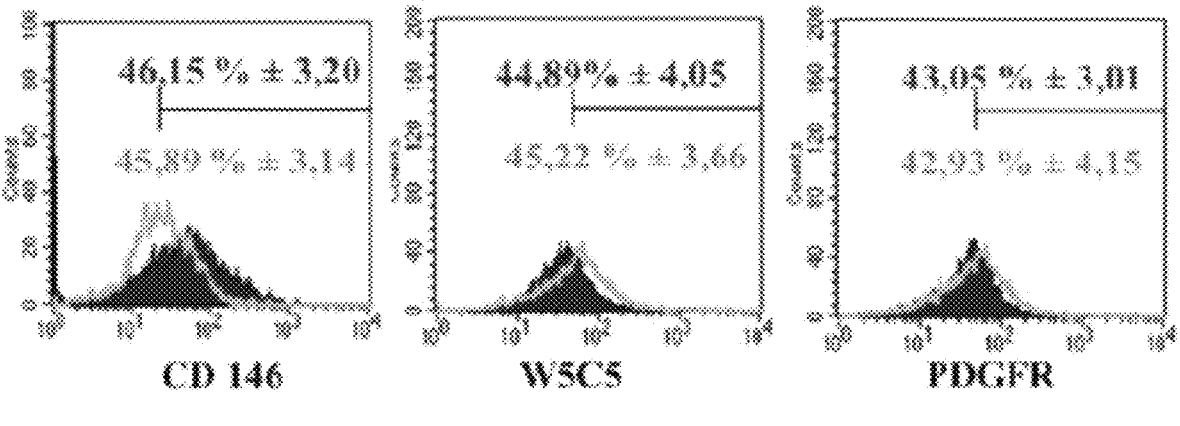
FIG. 5A                    FIG. 5B                    FIG. 5C
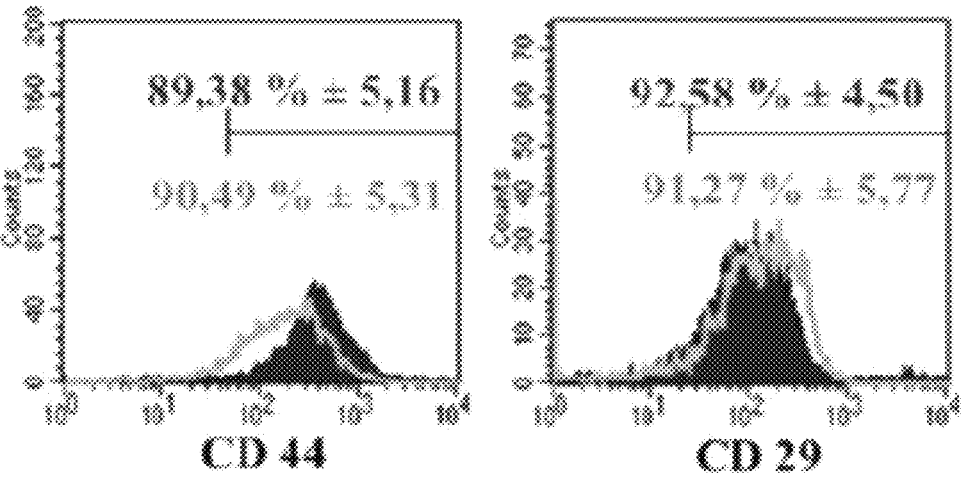
FIG. 5D                    FIG. 5E

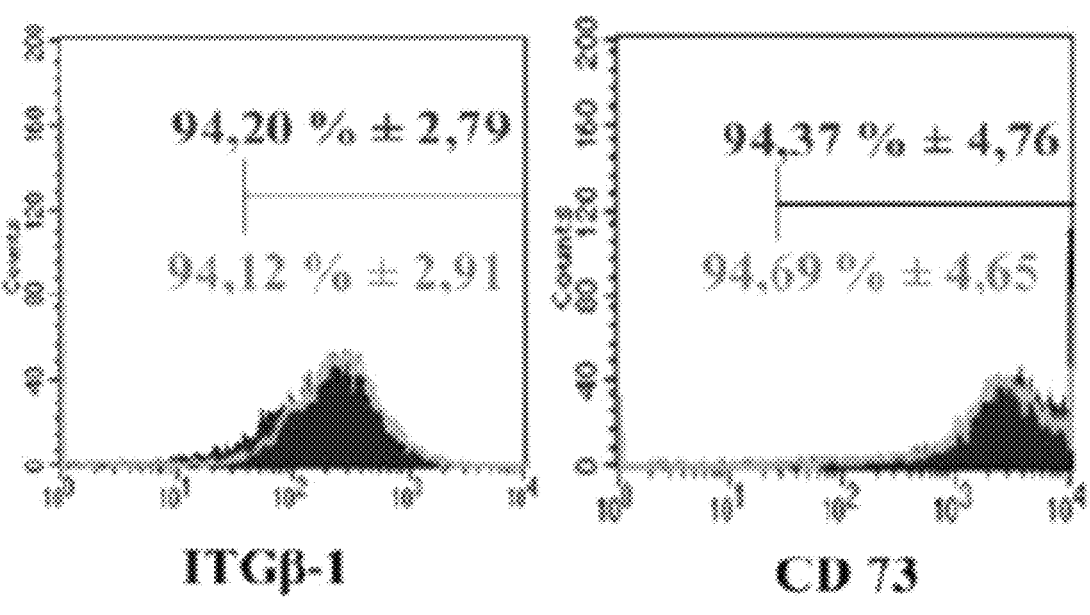
FIG. 5F                    FIG. 5G
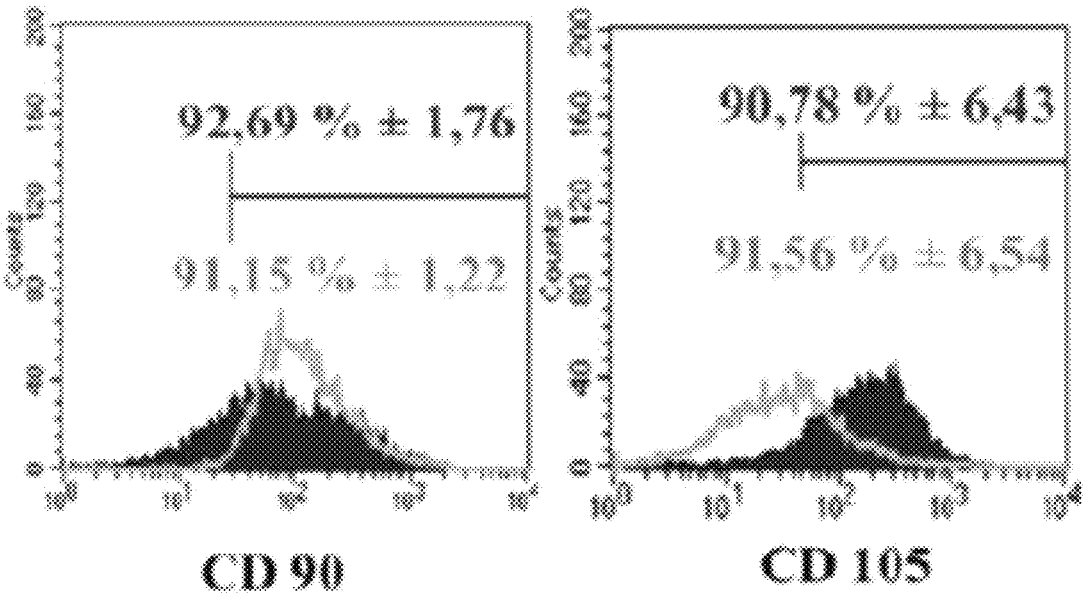
FIG. 5H                    FIG. 5I

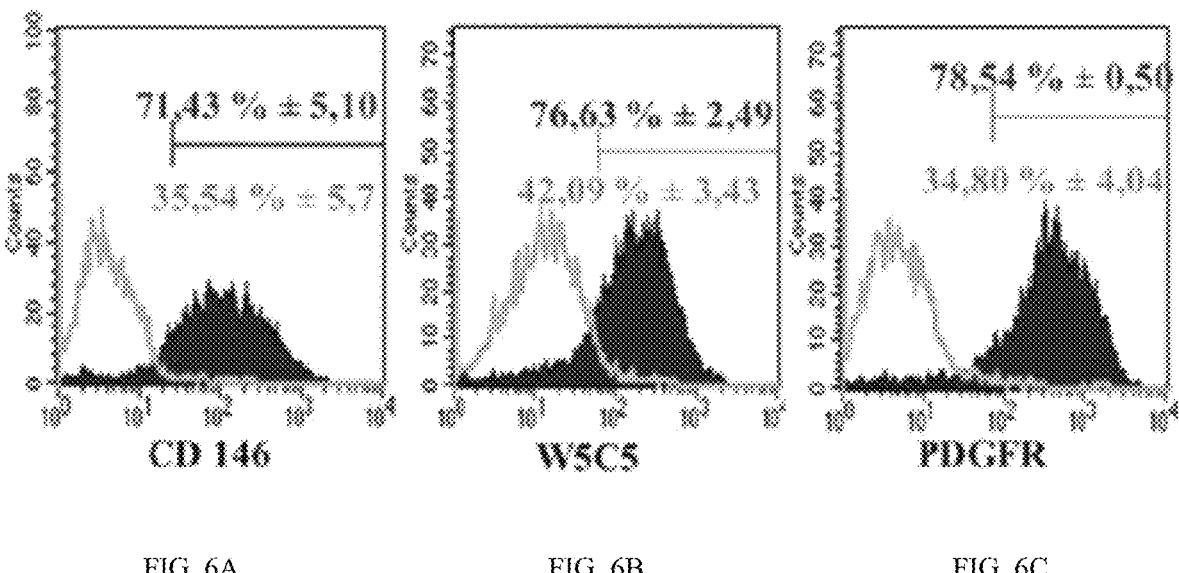
FIG. 6A                    FIG. 6B                    FIG. 6C
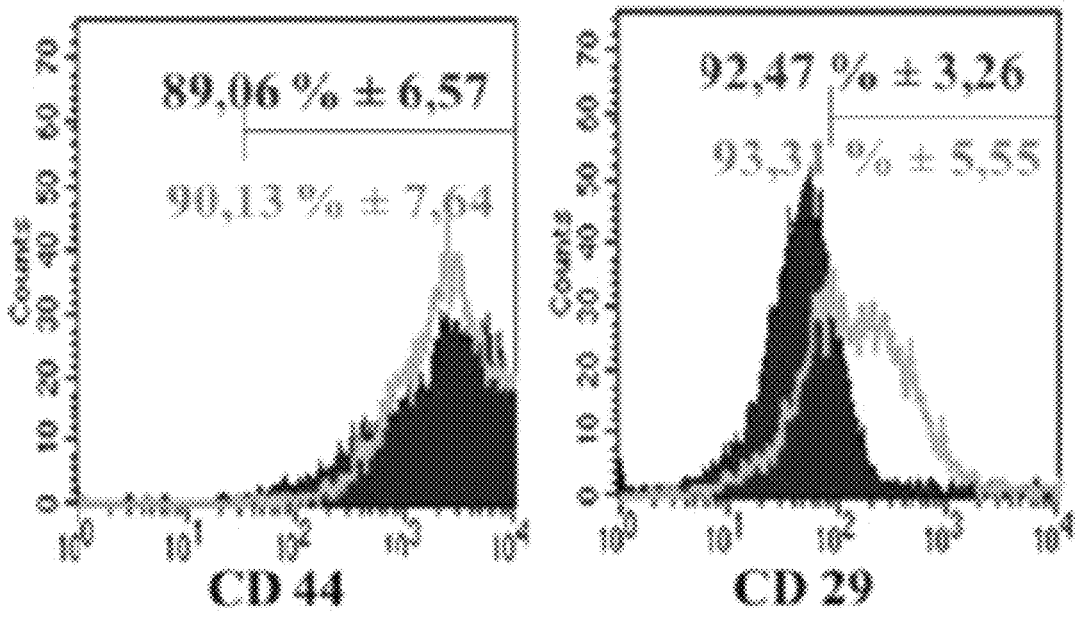
FIG. 6D                              FIG. 6E

BIOLOGICAL MARKERS IN THE DIAGNOSIS OF ENDOMETRIOSIS

CROSS REFERENCE TO THE RELATED APPLICATIONS

This application is the national phase entry of International Application No. PCT/TR2022/050458, filed on May 20, 2022, which is based upon and claims priority to Turkish Patent Application No. 2021/008431, filed on May 21, 2021, the entire contents of which are incorporated herein by reference.

TECHNICAL FIELD

The present invention relates to the combinations of the novel biological markers that can be used in the diagnosis of endometriosis.

BACKGROUND

Endometriosis is a disease defined as the implantation of the endometrial tissue, which lines the inner layer of the uterus of women of reproductive age and is lost upon thickening every month during menstruation since the adolescence period, outside of the uterus to the other parts of the body [1], [2]. Considering the prevalence of endometriosis, it is seen in 10-15% of reproductive age women and 9-50% in the infertile groups. although these values might increase up to approximately 50% in adolescents with the chronic pelvic pain and dysmenorrhea complaint [3]. Clinical symptoms such as headache [4], arthralgia, myalgia [5], allergies, hypothyroidism, fibromyalgia, chronic fatigue syndrome [6] and predisposition to vaginal yeast infection [7] are common in the endometriosis disorder. These symptoms related to the disease significantly affect the women's daily life activities and reduce their life quality [8] and furthermore this disease might even cause infertility in women, making them feel inadequate. At this point, it is essential to apply novel diagnosis and treatment methods for endometriosis to improve the quality of daily life of the patients and to relieve the patients psychologically.

Previous studies in the literature and the report published by American Society for Reproductive Medicine have shown that "laparoscopy", i.e., surgical intervention, has become the "gold standard" in the diagnosis of endometriosis [9] and brings many risks with it. For example, in addition to the risks of every surgical intervention, risks such as injury to the intra-abdominal organs such as bladder, bowel, ureter and subsequent internal bleeding, reduced ovarian reserves with damage to the ovaries and reduced probability of fertility can be listed as the risks in endometriosis patients [10], [11]. In particular, the surgical intervention poses a high risk in patients whose priority is to overcome the infertility factor caused by endometriosis [11]. Although monoclonal antibody of CA125 glycoprotein, which is one of the serum markers, is used in the diagnosis of endometriosis, it has been determined by studies that the results of this marker are questionable and its sensitivity is low, especially in endometriosis types that have spread to the peritoneal region [12].

Accumulating evidence in the literature suggests that there is a need for alternative diagnosis methods instead of the current diagnosis techniques with low-sensitivity, which have high costs and cause complications that the patient may experience after the surgery and prevent the patient from returning to social life in a short time. In light of these information, in the study, which is the subject of the patent application, it is aimed to define biological markers necessary for developing a novel diagnosis technique for endometriosis, which is cost-effective, painless and will not exhaust the patient psychologically with a concept such as "surgery".

Endometriosis disease is named after the "endometrium" and although endometriosis was described in 1860 [1], its etiology and pathogenesis are still unclear today [13], [14]. Different identification tables and theories have been created in the pathogenesis of endometriosis. These are retrograde menstruation/transplantation [2], [15], coelomic metaplasia [16], cellular immunity change [17], [18], [19], [20], metastasis [21], genetic factors [22], [23], environmental factors [24] and the interaction of specific genes with the environment [25]. The most emphasized theory introduced in the 1920s, states that the disease develops from the spread of endometrial tissue into the peritoneal cavity by retrograde menstruation [2], [18]. The presence of endometrial tissue in the form of subperitoneal implants indicates a pathological condition. This causes the attachment of the refluxing endometrial tissue fragments to the peritoneal surface, followed by the initiation of invasion and the development of the disease. According to Sampson, there are viable cells still living in the menstrual blood, which must be discarded with the menstrual cycle every month. He proposed that these viable cells can migrate to different regions instead of being discarded from the body, adhere to the region and to other neighboring organs they have migrated to and proliferate [2]. The human endometrium structure, which Sampson mentioned in his studies, and which was also the subject of the studies conducted later in the literature, has a chimeric cell population consisting of many different cell types [26]. In this chimeric structure, there are stromal cells, fibroblasts, endothelial cells, lymphoid cells, and smooth muscle cells and mesenchymal stem cells surrounding the endometrial wall. It has been hypothesized that endometrial stem cells are shed together with their niche cells into the peritoneal cavity through retrograde menstruation in women who develop endometriosis [27], [28], [29], [30] and this was found to support Sampson's theory. In animal experimental studies, it has been shown that mesenchymal stem cells isolated from menstrual blood taken from baboons with continuing menstrual cycle could induce experimental environment for the development of endometriosis [31]. The fact that the adhesion and migration properties are high in endometrial mesenchymal cells (eMSC) has led to the idea that tissue transglutaminase (TG2) enzyme loses its cross-linking property and is highly synthesized in these cells as a specific cell adhesion molecule [32], [33], [34], [35], [36] and it is hypothesized that thus the cells that should be located in the endometrium have the ability to migrate to other locations to create endometriosis. In line with this information, differences in the surface markers of eMSCs, which are abundant in the chimeric structure of the endometrium and have a high potential to migrate between healthy and endometriosis patients, were examined and determined.

SUMMARY

The objective of the invention is to list the possible biological markers that are expressed differently in eMSCs isolated from endometrial biopsy samples in the diagnosis of endometriosis compared to healthy eMSCs. Biological markers selected from the list of markers whose expression was observed to change in eMSC samples of 5 patients were also pathologically evaluated in the endometriosis focal tissues of 17 patients diagnosed with endometriosis and then identified as biomarkers.

Another objective of the invention is to develop a diagnosis kit, in which gene or protein expressions of tissue transglutaminase (TG2), cluster of differentiation 146 (CD146), platelet derived growth factor receptor (PDGFR), Integrin Beta 1 and Sushi domain containing protein 2 (SUSD2, or also synonymously called W5C5) markers that are differentially expressed in endometriosis eMSCs, are used alone or in combination.

In this way, it would be possible to make a diagnosis with a biopsy sample instead of the surgical diagnosis that is currently required for the definitive diagnosis of endometriosis in patients.

BRIEF DESCRIPTION OF THE DRAWINGS

The invention titled "NOVEL BIOLOGICAL MARKERS IN THE DIAGNOSIS OF ENDOMETRIOSIS", developed to achieve the above mentioned objectives, is illustrated in the accompanying figures, in which:

FIGS. 2A-2M show the characterization of patient endometrial mesenchymal stem cells (peMSCs) from endometrial tissues taken from five different patients with endometriosis diagnosis by flow cytometry is represented by a black filled curve and ±values represent the standard deviation for 5 different peMSCs. Cells incubated with isotype IgG antibody were used as negative control (NC) and represented by a hollow gray curve.

FIGS. 3A-3C show TG2 protein level in all isolated eMSCs. Where FIG. 3A shows TG2 protein bands in five different groups were visualized by Western Blot technique. FIG. 3B shows the analysis of TG2 protein isolated from different control (heMSC) and patient (peMSC) mesenchymal stem cells of five different groups. FIG. 3C shows the mean value and statistical analysis of TG2 protein isolated from different heMSCs and peMSCs of five different groups. All cells used were at passage 3 and isolated by the non-enzymatic procedure. The value of P<0.0001 is symbolized by ****.

FIG. 4A shows membrane images of the results of SCR and shRNA results applied to control and patient samples in five different groups. FIG. 4B shows the analysis of SCR and shRNA applied to each control and patient sample in five different groups. FIG. 4C shows the mean average values of the analysis of SCR and shRNA applied to control and patient samples in five different groups. As a result of the statistical analysis, statistically non-significant p value is denoted by "ns", while significant p<0.00001 value is denoted by *****.

FIGS. 5A-5M show the mean (±) values and standard deviations of flow cytometry of control (heMSCs) and control treated with scrambled shRNA (heMSCs+SCR) in all groups. While five different heMSC samples are represented by black filled curve, heMSC+SCR samples are symbolized by hollow gray curve in the graph.

FIGS. 6A-6M show the mean (±) values and standard deviations of flow cytometry of peMSC+SCR treated with scrambled containing control lentiviral particles and TG2 targeting shRNA-treated peMSC+shRNA samples of all groups. While five different heMSC samples are represented by black filled curve, heMSC+SCR samples are symbolized by hollow gray curve in the graph.

DETAILED DESCRIPTION OF THE EMBODIMENTS

Figures 1A, 1B, 1C, 1D, 1E:
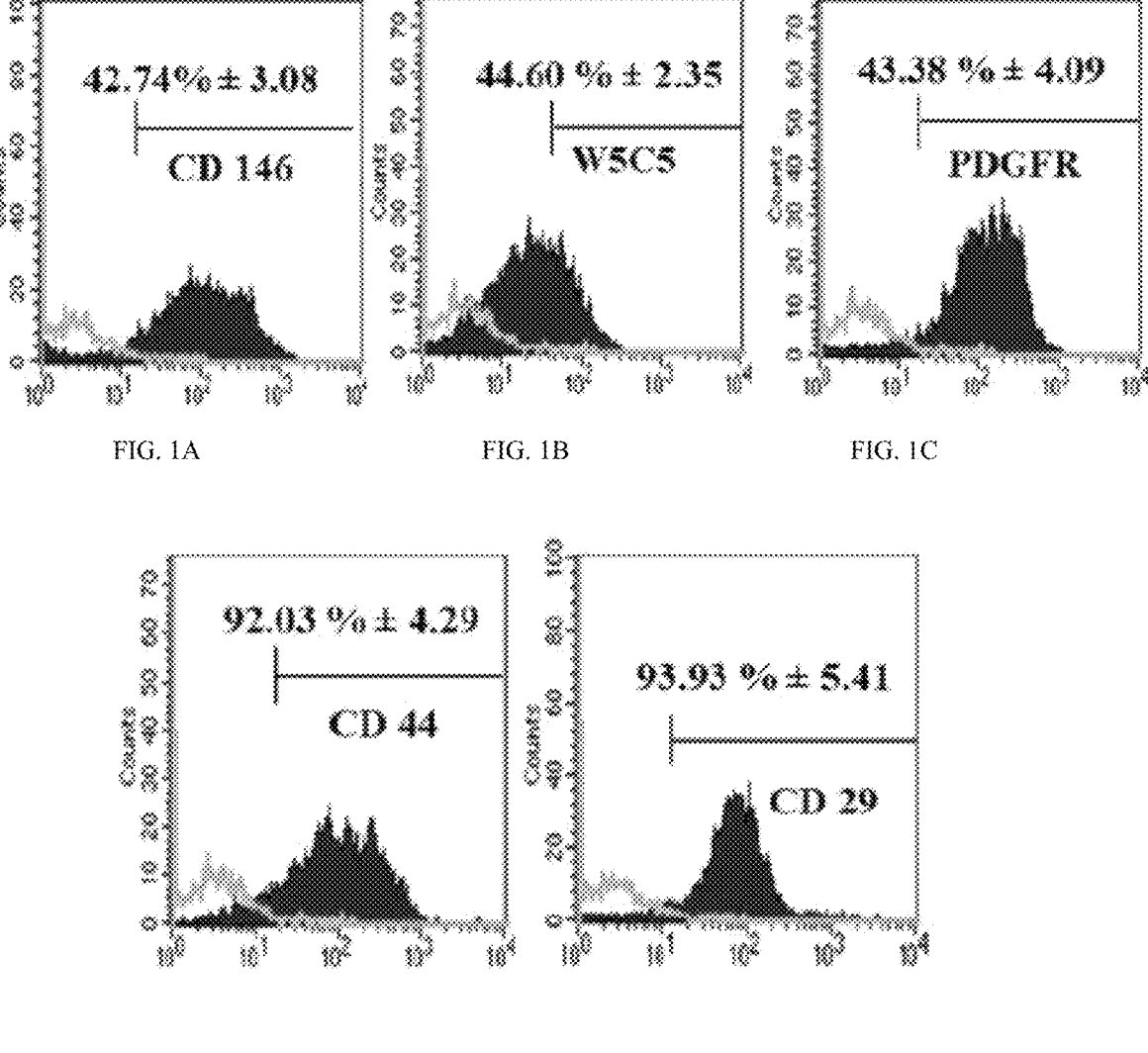
FIGS. 1A-1M show the characterization of healthy control endometrial mesenchymal stem cells (heMSCs) from endometrial tissues taken from individuals without endometriosis diagnosis by flow cytometry is represented by a black filled curve and ±values represent the standard deviation for 5 different heMSCs. Cells incubated with isotype IgG antibody were used as negative control (NC) and represented by a hollow gray curve.
Figures 1F, 1G, 1H, 1I:
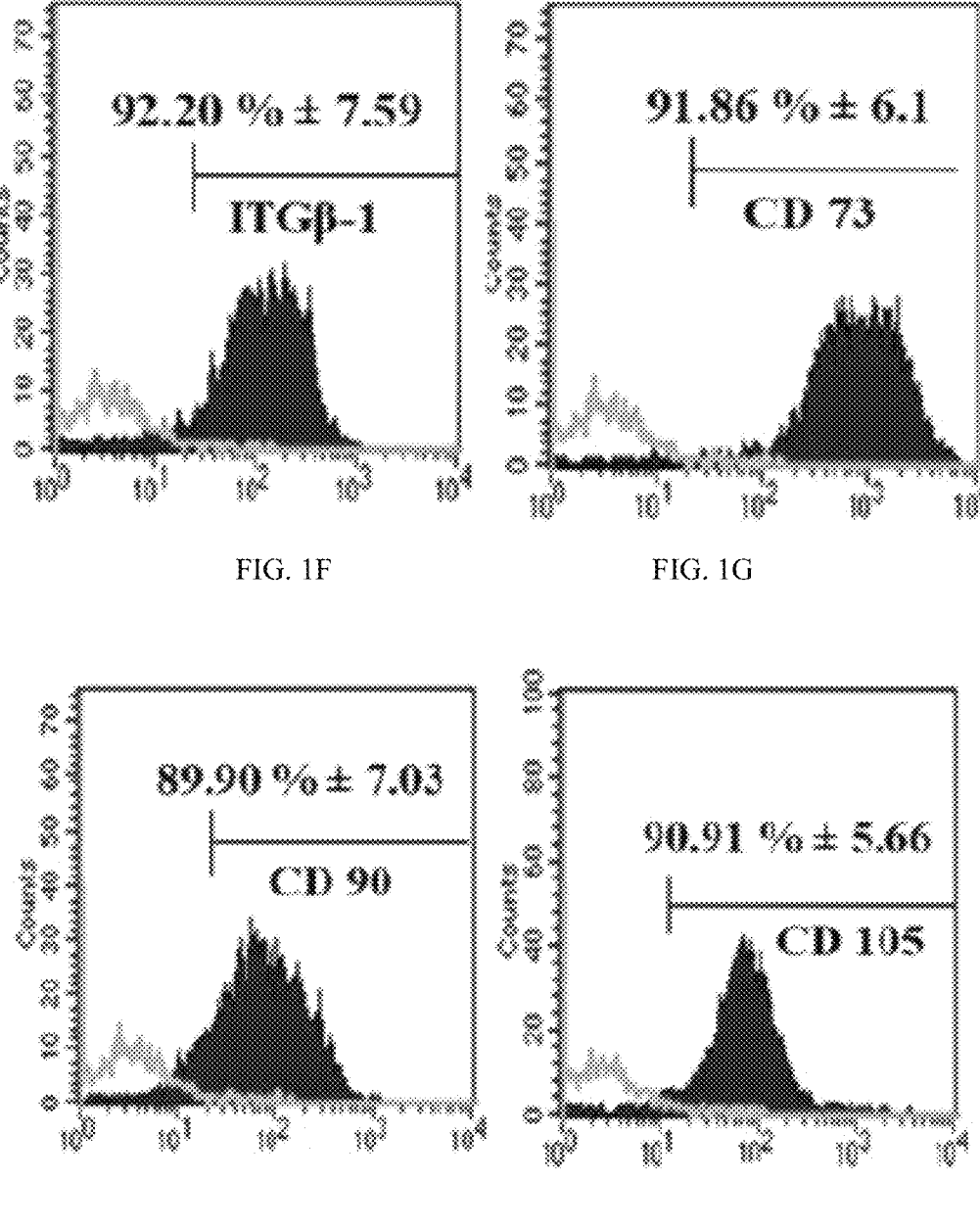
Figures 1J, 1K, 1L, 1M:
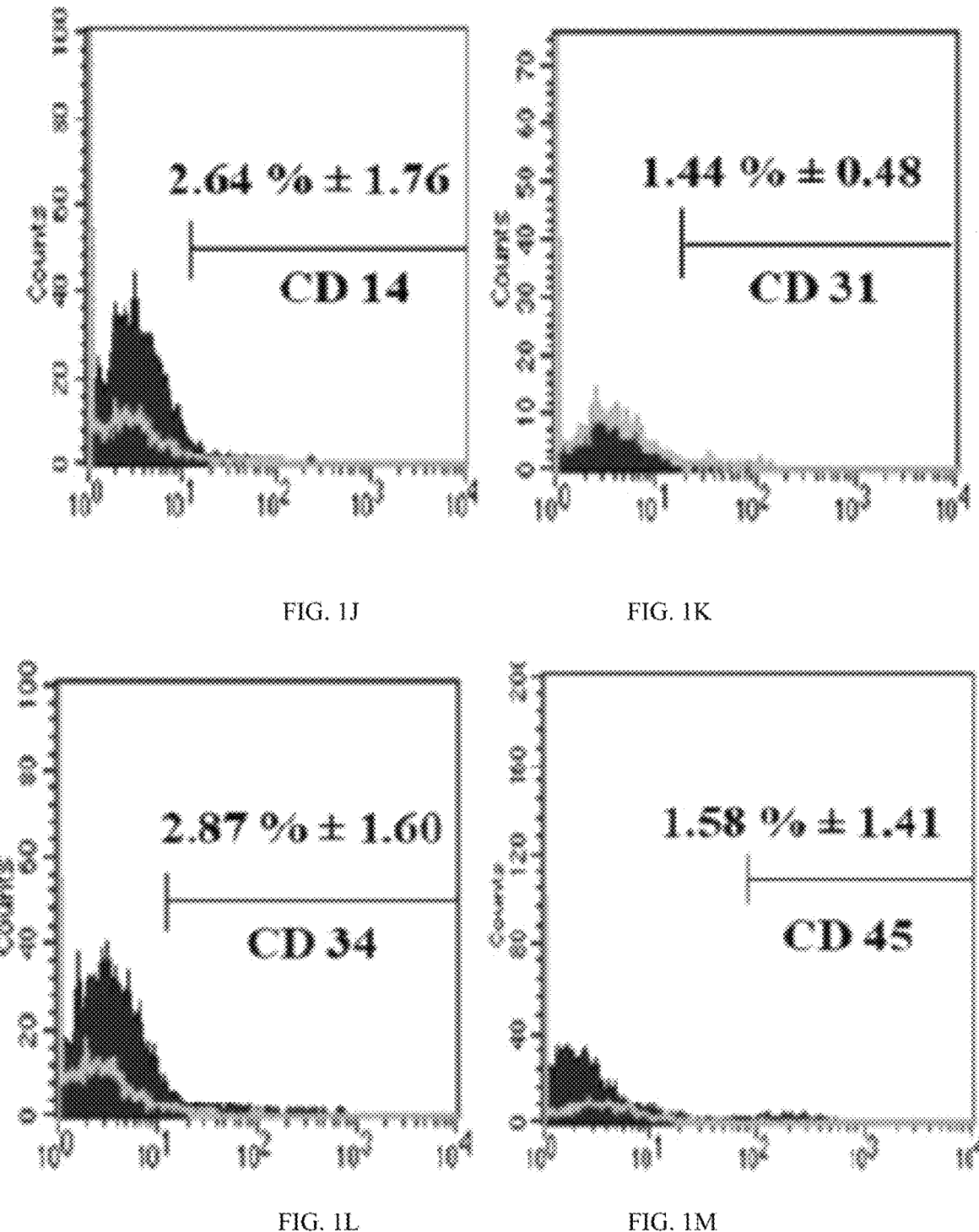
Figures 2A, 2B, 2C:
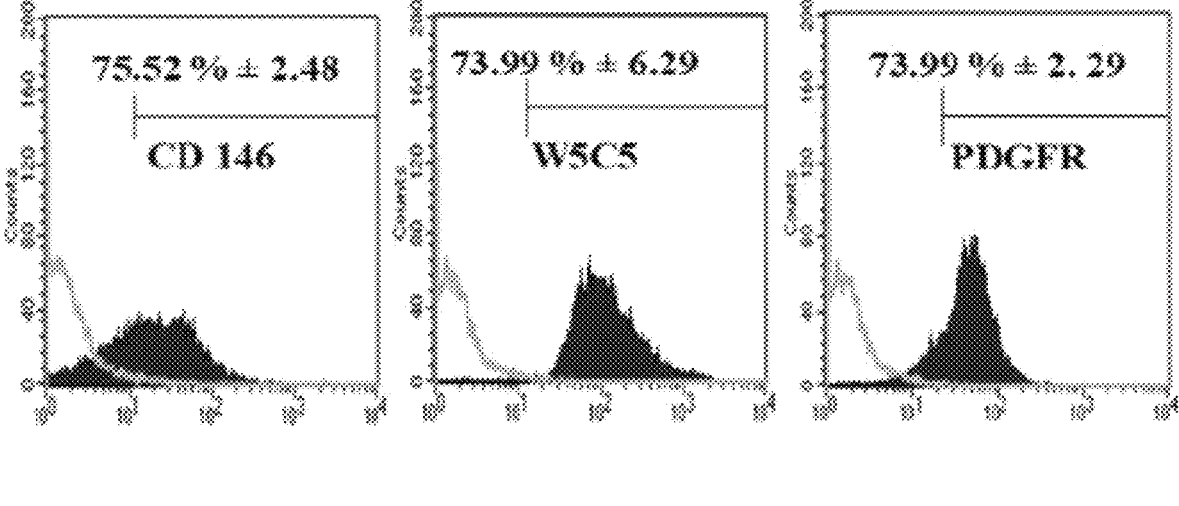
Figures 2D, 2E:
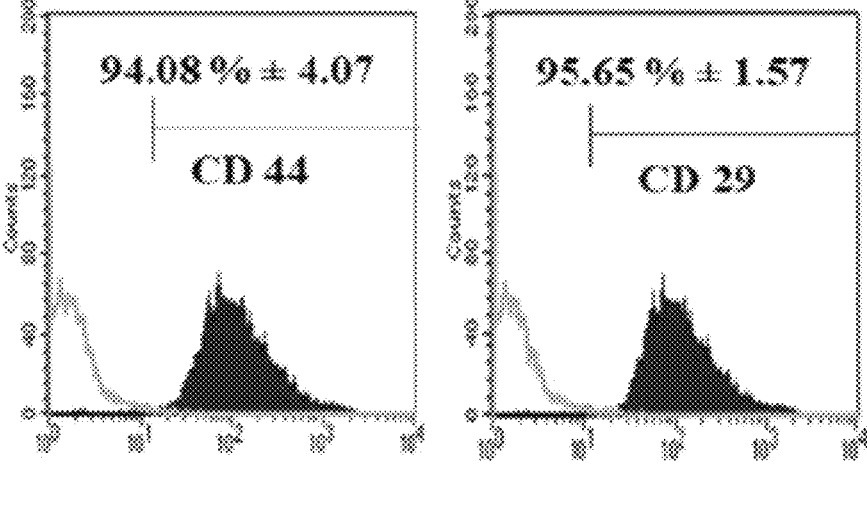

The subject of the invention is the use of tissue transglutaminase (TG2) as a biomarker for the diagnosis of endometriosis in isolated endometrial mesenchymal stem cells derived from endometrial biopsy and/or menstrual blood from endometriosis patients. This method is a non-invasive method compared to the "laparoscopy" method used in the diagnosis of endometriosis today. In addition to this, together with the tissue transglutaminase (TG2), at least one marker selected from a group consisting of "cluster of differentiation 146" (CD146), "Sushi domain containing protein 2" (SUSD2, also synonymously called W5C5), "integrin beta 1 (ITGB1)" and "platelet derived growth factor receptor" (PDGFR) markers and combinations thereof, are used as a biomarker for the endometriosis diagnosis in isolated endometrial mesenchymal stem cells derived from endometrial biopsy and/or menstrual blood from endometriosis patients. Furthermore, an endometriosis diagnosis kit, which comprises TG2 or markers of the invention in combination with one or more of CD146, SUSD2 (W5C5), ITGB1 and PDGFR, alone or in combination with each other and which is used for the measurement of gene and/or protein levels thereof in "endometrial mesenchymal cells (eMSC) isolated from endometrial biopsy sample and/or menstrual blood", is developed within the scope of invention. In addition to these, the gene and protein expression levels of the markers of the invention, which are TG2 or a combination thereof with one or more of CD146, SUSD2 (W5C5), ITGB1 and PDGFR, in mesenchymal cells isolated from menstrual blood can be also used for detecting the success of drugs used in treatment and the course of treatment. Given that endometriosis accounts for 9%-50% of infertility cases, it is of great importance to determine the infertility risks of young women due to endometriosis. Taking into consideration that the surgeries, which are performed when the endometriosis cysts reach large sizes, significantly reduce the ovarian reserve, preserving the fertility of the patients by oocyte cryopreservation method at young age will become applicable with the early and easy diagnosis of endometriosis that will be developed within the framework of the invention.

Endometriosis is named after the "endometrium", which means the layer that lines the inner layer of the uterus of women of reproductive age and is lost upon thickening every month during the menstruation. In endometriosis, the tissue resembling the endometrium, which should normally be present in the inner layer of the uterus, grows outside the uterus and is implanted in other parts of the body [37]. As the ectopically implanted tissue contains viable endometrium cells, in every menstrual period they function the same way as the cells in uterus [37]. The high adhesion and migration properties of these cells can be explained by the adhesion and migration inducing surface proteins they express on the cell surfaces. In the literature, it has been shown that different from mesenchymal stem cells isolated from other organs, eMS cells express CD146, PDGFR, W5C5 markers [38]. We recently published in a conference abstract that tissue transglutaminase (TG2) protein is also expressed in eMS cells in addition to these markers [39]. In our conference abstract, TG2 enzyme activity and mRNA levels along with the levels of syndecan-4 and integrin beta 1 were analyzed and the effect of TG2 on matrix metaproteinase enzyme activity was determined in eMS cells isolated from a healthy individual and a patient. In laboratory studies, which we conducted as a continuation of our conference abstract and which is the subject of this patent application, it has been shown that the increased TG2 not only controls the protein expression of CD146, SUSD2 (W5C5), ITGB1 and PDGFR but also promotes eMSC proliferation in eMSCs from five endometriosis patients. In addition, the upregulation of TG2 together with CD146, ITGB1 and PDGFR was also evident in 17 biopsy samples obtained from endometriosis tissues. Like other members of the family, human tissue transglutaminase (TG2), a member of the transglutaminase family, catalyzes $Ca^{+2}$-dependent protein deamidation, transamidation, and cross-linking [40], [41]. The transamidase activity of TG2 plays an extracellular role in matrix stabilization, which is essential in wound healing, angiogenesis, and bone repair, and generally plays an intracellular role in cross-linking of the proteins during apoptosis [40]. Since the discovery of TG2 in 1957, its numerous enzymatic substrates have been identified in intracellular compartmentations including the cytosol, nucleus and mitochondria, as well as in extracellular compartmentations within the intracellular and extracellular matrix (ECM) [42], [43], [44]. In addition to $Ca^{2+}$-dependent post-translational modification of proteins, the enzyme, also known as TG2, cytosolic type II or liver transglutaminase, can bind and hydrolyze GTP and act like a G protein [41], [45] Therefore, in terms of catalytic activity, TG2 can be termed as a bifunctional enzyme due to its ability to catalyze $Ca^{2+}$-dependent protein crosslinking activity and $Ca^{2+}$-independent GTP hydrolysis [41], [46], [47], [45], [48].

In the $Ca^{+2}$-dependent transamidation reaction of TG2, an intermolecular isopeptide ε-(γ-glutamyl) lysine bond is formed, and this causes internal cross-linking of monomeric protein units [49]. These bonds are resistant to chemical and physical degradation; thus, they are known to have a biological importance, particularly in the stabilization of the extracellular matrix (ECM) [50], [51]. Studies have shown that TG2 turns into a protein that plays an active role in cell adhesion and migration as a G protein [41], [45], when TG2, which is dependent on the $Ca^{+2}$ level in the transamidation reaction, loses its cross-linking activity at low $Ca^{+2}$ amount [36], [50], [52]. The ability of TG2 to function in the adhesion function depends on its cooperation with two transmembrane proteins, integrins (β1/β3/β5) and syndecans, as well as non-covalent binding of ECM proteins to the adhesion receptor as a result of this cooperation [50], [53]. Both these receptors and TG2 itself interact with fibronectin [34], [36], [50]. In recent studies, it has been suggested that TG2 loses its "cross-linking" enzyme activity by binding to the fibronectin (FN) matrix protein extracellularly and acts as a novel cell adhesion protein that functions as a coreceptor for integrin and syndecan-4 receptors [32], [33], [34], [35], [36]. In addition, TG2 in complex with FN matrix protein, has a role in preventing cells whose integrin receptors are blocked and which could not bind to a surface, from undergoing apoptosis [54], thus upregulation of TG2 was observed in melanoma, breast, lung and pancreatic cancers and it was proven that TG2 confers drug resistance and metastatic properties to cancer cells [55], [56], [57], [58], [59], [60], [61], [62].

According to the retrograde menstrual cycle in endometriosis patients, CD146, PDGFR, W5C5 surface markers are other molecules that may play a role in the migration of endometrial cells to the peritoneum and organs in the abdominal cavity as a result of the reverse flow of the endometrial cells during menstruation. In the laboratory studies we conducted within the framework of our patent application, eMSCs isolated from individuals with endometriosis and eMSCs isolated from healthy individuals were compared and it was detected that CD146, PDGFR, W5C5 surface markers were expressed at a higher rate in endometriosis eMSCs than in healthy ones. Increased expression of these markers in eMSCs was shown to be controlled by TG2 where TG2 expression is silenced by shRNA technology.

Although in many studies in the literature, cells that displayed increased expression of CD146, a member of the immunoglobulin superfamily (IgSF) which act as a cell adhesion molecule (CAM), showed increases in cell migration and invasion potential [63], [64], this marker has not been studied previously in endometriosis patients except healthy eMSCs. In addition to CD146, another endometrial mesenchymal cell marker PDFGR was found to be overexpressed in endometriosis mesenchymal stem cells (peMSCs) when compared to healthy endometrial mesenchymal stem cells (heMSCs), suggesting this marker to be considered in our hypothesis as another potential parameter. Studies have shown that PDFGR is highly expressed in ovarian [65], [66], [67], [68] and uterine [69] cancers, which are developed in untreated late-phase endometriosis cases. It is also stated in studies in the literature that PDGFR is essential in various cellular processes such as cell proliferation, migration, transformation and survival during the development and pathogenesis of various endometrial diseases [70], [71], [72]. However, although it has been elucidated that PDFGR plays a role in the development of many different gynecological disorders, a comparative study of eMSCs of individuals with/without a previous diagnosis of endometriosis has not been performed. This deficiency in the literature covers another original study of our invention. As expected in the light of this information and shown by the results of the present invention endometriosis cells contain higher PDGFR than healthy cells. In addition to these markers, another marker is an antibody which is known as W5C5 that recognizes SUSD2 protein which is shown to be specific to endometrial mesenchymal cells isolated from healthy individuals. Just like CD146 and PDGFR, this marker is also known to be expressed at basal level in endometrial mesenchymal stem cells [38]. Garget et al. showed in their studies that W5C5 is highly expressed in perivascular implantation foci in endometriosis patients [73], [74]. In another study in the literature, W5C5 levels were also found to be higher in fibroblast cells isolated from individuals who were diagnosed with endometriosis, compared to fibroblast cells isolated from healthy individuals [75]. The detection of W5C5 levels in eMS cells isolated from healthy and endometriosis patients carried out within the scope of the invention has never been studied in the literature.

Within the framework of our invention, the following have been demonstrated by our studies conducted on endometriosis and healthy eMSCs:

3. expression of CD146, PDGFR and W5C5 is increased in endometriosis eMSCs under TG2 control; and 4. TG2 is the main actor in driving the proliferation of these cells.

In addition to our studies with CD146, Integrin β-1, PDGFR, TG2 and W5C5 markers in endometrial MSCs, the expression levels of these markers were investigated in the endometriosis foci taken from different regions of 17 patients in different stages by immunohistochemical staining method. Staining in glands and stroma in the tissues were evaluated individually and it has been detected that as we have shown in eMSCs, CD146, PDGFR and TG2 markers were expressed more than 50% in the glands of all endometriosis focal tissues, as intense (++) or very intense (+++) (Table 5). It has been detected that CD146, PDGFR and TG2 expressions in the stroma were lower than those in the glands in the endometriosis focal tissues.

Experimental Study

Determination of Cell Groups to be Used in Experiments

All isolated cells used in our experiments were isolated from tissue samples of patients diagnosed with endometriosis and healthy volunteers. Ethics committee application of our study was made to Yeditepe University Human Ethics Committee and approval numbered Decision No: 63/509 was obtained from the committee members. In the experiments carried out within the framework of our invention, tissue samples taken from five different healthy people (control groups) and five different patients diagnosed with endometriosis were studied. Healthy tissue samples used in the study were obtained from fertile women under 49 years of age without endometrial polyps in the uterus, endometrial hyperplasia, endometrial cancer or submucosal myoma and who were not diagnosed with endometriosis. Endometrial biopsy samples from healthy patients were collected during non-gynecological surgeries from fertile individuals who did not have endometriosis in the pelvic peritoneum and organs.

Patient samples were voluntarily collected from women under the age of 49 with confirmed diagnosis of moderate or severe endometriosis according to American Society for Reproductive Medicine (ASRM) classification system. All patients were undergone laparoscopic intervention for abdominal cavity examination and total endometriotic tissue excision. Women with pathological diseases other than endometriosis, which may affect the results of the study were not included in the study.

Cell Isolation and Culture

After the collected endometrial tissues were transferred to our laboratory in serum physiological saline, they were rinsed 3 times with phosphate buffer solution (PBS) containing 3% (v/v) penicillin streptomycin for removal of the blood in the tissues and sterilization. After the samples were washed 2 times with serum-free growth culture medium MEM, tissue pieces were then minced into 1-2 mm$^3$ pieces with the help of scalpel. Following this process, the minced tissue pieces were stirred at 70 rpm for 2 hours at 37° C. in 10 ml of serum-free MEM containing 0.05% trypsin enzyme. Following the stirring process, the cells were centrifuged at 1500 rpm for 5 minutes and then supernatant was discarded, the remaining pellet portion was transferred to 6-well cell dishes, and a coverslip was placed thereon, and cells were left to grow in low glucose (1 g/L) DMEM culture medium containing 20% (v/v) fetal bovine serum (FBS), 100 IU/ml penicillin, 100 μg/ml streptomycin at 37° C. and 5% CO2-humidified environment for 5 days. At the end of the incubation period, the cells covering the surface of the 6-well plate were transferred to T-25 and then T-75 tissue culture dishes where they were grown, and then they were subjected to CD marker analysis for the characterization of stem cell properties.

Characterization of eMSCs

Flow cytometry analysis was applied for the characterization of control and patient eMS cells. The cells were fixed with 4% (v/v) paraformaldehyde solution and then were washed 3 times with PBS, and labeled with CD146, PDGFR, W5C5, CD44, CD29, CD73, integrin β-1, CD90 and CD105 antibodies, which are surface markers for eMSCs, for 16 hours at 4° C. and analyzed using flow cytometry. At the same time, the isolated cells were also incubated with CD31, CD34, CD45 antibodies, which are hematopoietic stem cell surface markers (to act as a negative control). The cells were precipitated at 300×g and then washed once with PBS and suspended in 1 ml PBS, and analyzed using the FL1 (green), FL2 (red) channels on the flow cytometer.

Western Blot

TG2 protein level in heMSC, peMSC and cells treated with shRNA to downregulate TG2 was detected by Western blot method. Beta actin was used as the control antibody to show that protein amount of each sample was loaded equally. For this purpose, eMSCs were seeded into 6-well plates at a density of 300,000 cells per well for 4 hours. Following the incubation period of 24 hours, 30 μl of RIPA buffer (1 mM PMSF, 0.5% Non-idet, 0.1% SDS, 1 mMNaF, 1 mM Na3VO4 and protease inhibitor cocktail) was added onto the cells, and the cell membranes were fragmented, and cell lysates were obtained and the protein amount was determined by Lowry's method. Proteins (50 μg/well) in the cell homogenate were separated by sodium dodecyl sulphate-polyacrylamide gel electrophoresis (SDS-PAGE) technique in gels with densities ranging from 8% to 12%. Proteins were transferred to nitrocellulose membrane at 200 mA current for 1 hour by wet-transfer method and then the membranes were kept in Tris-Tween (100 mM Tris-HCl, 0.9% (w/v) NaCl and 0.05% (w/v), pH 7.4) solution containing 5% milk powder for 1 hour and incubated with the appropriate antibodies at 4° C. for 16 hours. Antibodies used in Western Blot were prepared in Tris-Tween solution containing 5% milk powder at the concentrations indicated according to the purchaser's recommendation. Following an incubation period of 16 hours, the membranes were washed three times for 5 minutes with Tris-Tween solution and labeled with HRP-labeled anti-mouse antibody 1:5000 or 1:1000 diluted in Tris-Tween solution containing 5% milk powder for 2 hours at room temperature. At the end of 2 hours, the membranes, each of which were washed with Tris-Tween solution three times for 5 minutes, were kept in ECL-HRP substrate solution and then photographed with ChemiDoc XRS+ (BioRad) device.

Reduction of TG2 Expression by shRNA Technology

After 24 hours following being seeded in 24-well plates (20,000/well), eMSCs were kept in culture medium containing 4% (v/v) FBS, 100 IU/ml penicillin, 100 μg/ml streptomycin (transduction culture medium) and 8 μg/ml polybrene for 12 hours. While peMSCs were infected with lentiviral particles containing shTG2 and control shRNA lentiviral particles, which were diluted in transduction culture medium to a multiplicity of infection (MOI) of 4, heMSCs were only transduced with control shRNA using MOI of 2. Viral particles were produced by Santa Cruz (USA) company and shTG2 viral particles comprise target-specific shRNA with a length of 19-25 nucleotides (+hairpin) that binds to TG2 mRNA in at least 3 different locations. The control shRNA comprises the scrambled shRNA sequences within the lentiviral particles that will not cause any particular disruption of any cellular message and was used to determine whether the transduction process has any effect on eMSC. After the treatment, the cells were washed once with PBS and then kept in culture medium containing 12% (v/v) FBS, 100 IU/ml penicillin, 100 µg/ml streptomycin and 2.5 µg/ml puromycin for 6 to 9 days. Since the puromycin resistance gene is also encoded in plasmids containing shRNAs, cells transduced with the shRNA plasmid are expected to develop puromycin resistance. At the end of the puromycin selection, cells were cultured and banked in liquid nitrogen in FBS containing 10% (v/v) dimethyl sulfoxide (DMSO).

Determination of Cell Proliferation Capacity by WST-1 Assay

2-[4-iodophenyl]-3-[4-nitrophenyl]-5-[2,4-disulfophenyl]-2H tetrazolium monosodium salt water soluble tetrazolium (WST-1) assay, is a colorimetric measurement used for testing the TG2-driven proliferation of eMS cells at time periods of 24, 48, 72 and 96 hours, respectively, that was performed on all isolated eMS cells with/without shRNA [76]. In the working principle of WST-1 cell proliferation assay, mitochondrial activity of cells is measured. First, cells were incubated with WST-1 reagent, which is a colorimetric substrate [77]. This technique is based on the reduction of tetrazolium salts catalyzed by mitochondrial enzyme systems. First, early in the morning, all isolated eMSCs were seeded into a 96-well plate at 2000 cells/well, 5000 cells/well, 10000 cells/well, 15000 cells/well and 20000 cells/well to construct a standard curve. After this process, all isolated eMSCs were seeded into a 96-well plate at 2000 cells/well and at the designated time points cells were incubated with a mixture containing 5 µL of WST-1 reagent and 45 µL of growth medium for 1 hour. At the end of the incubation period, the proliferation capacity of the cells was determined by measuring the absorbance of the cells at a wavelength of 420-480 nm (λ max 450 nm).

Selecting the Tissue Sections Taken from Endometriosis Foci

The reports of the samples of the patients diagnosed with endometriosis were scanned by the pathologist and 17 patient samples in different stages were selected. The requirement of samples to be from different stages was laid down as a condition for the selection criteria. Tissue samples were stored in a paraffin-embedded manner after they were collected from the patient.

Immunohistochemical Staining of the Tissue Sections

Paraffin-embedded tissue samples were allowed to cool at −20° C. to take thin sections. Sections of 5 µm thickness were taken from the samples using a microtome device, floated on hot water and placed on positively charged slides. The slides were dried and the tissue section with paraffin was adhered to the surface of the slide. Before staining with the antibody, all slides were kept at 70° C. for one hour to remove the paraffin from the tissues. Then, they were prepared and treated with CD146, Integrin β1, PDGFR, W5C5 and TG2 endometrial mesenchymal stem cell surface marker antibodies as recommended by the manufacturer's instructions. All processes of immunohistochemical staining were performed with Leica Bond Max Immunocytochemistry Stainer (Shanghai, China) device. After the samples were completely dried in the device, mounting medium was added and covered with a coverslip. For each antibody staining of each sample, five images each were taken from different regions using the light module of Zeiss fluorescent microscope with a 40× objective.

Quantification and Evaluation of Immunohistochemical Staining Images

The staining intensity of each marker was analyzed separately for glands and stroma by using the ImageJ program and the staining intensities were indicated in percentage. Then, the weakest and most intense staining were selected, and the median value was calculated in the excel program. The staining values between the weakest staining and the median number were divided into two and evaluated as "0" and "+". Similarly, the values between the highest staining and the median number were divided into two and evaluated as "++" and "+++". The numerical evaluation table is as follows (Table 1). This process was performed for endometriosis foci from 17 patients. Since there was no staining in any of the studies performed with the W5C5 antibody, it was not included in the evaluation.

TABLE 1

| Evaluation of immunohistochemical staining | | | | |
|---|---|---|---|---|
| | CD146 | ITGβ-1 | PDGFR | TG2 |
| Percentage of minimum staining area | 1.597 | 1.063 | 1.653 | 5.420 |
| Percentage of maximum staining area | 66.363 | 34.107 | 47.492 | 72.996 |
| Percentage of median staining area | 22.550 | 8.655 | 16.499 | 35.986 |
| 0 | 1.597-12.074 | 1.063-4.859 | 1.653-9.076 | 5.420-20.703 |
| + | 12.074-22.550 | 4.859-8.655 | 9.076-16.499 | 20.703-35.986 |
| ++ | 22.550-44.457 | 8.655-21.381 | 16.499-31.995 | 35.986-54.491 |
| +++ | 44.457-66.363 | 21.381-34.107 | 31.995-47.492 | 54.491-72.996 |

Statistical Analysis

Graphs prepared for all data analyses were prepared in the GraphPath program and after determining whether the data had a parametric or non-parametric distribution, the data showing parametric distribution were analyzed by student-t test compared to the control. Anova and Mann-Whitney Tests were used for non-parametric data. Each experiment was repeated at least 5 times. $p<0.05$ was accepted as significant. ($*p\leq0.05$; $p\leq0.01$; $*p\leq0.001$; $****p\leq0.0001$).

Experimental Results

Our research, which is the subject of the invention, was carried out in the molecular cell biology research laboratories in the Department of Genetics and Bioengineering at Yeditepe University. Healthy endometrial mesenchymal stem cells (heMSCs) and endometriosis mesenchymal stem cells (peMSCs), which were isolated in cell culture medium from endometrial tissues collected from individuals who are diagnosed with endometriosis (patient groups) and who are not diagnosed with endometriosis (control groups), were used as the cell model. The experiments of the present invention were conducted by working with samples collected from five different patient groups and five different healthy groups, and all experiments were applied once for each tissue sample, and thus five repetitive sets of experiments were created. Flow cytometry analysis was applied for the characterization of eMS cells. By following the protocol explained in the characterization of eMSCs; CD146, PDGFR, W5C5, CD44, CD29, CD73, Integrin β-1, CD90, and CD105 antibodies were used as mesenchymal markers and CD31, CD34, CD45 antibodies were used as hematopoietic (to act as negative control) markers. In FIGS. 1A-1M, average binding affinities of CD markers for n=5 cells from each group with standard deviation were given.

In heMSC, 42.74% for CD146, 44.60% for W5C5, 43.38% for PDGFR, 92.03% for CD44, 93.93% for CD29, 92.20% for Integrin β-1, 91.86% for CD73, 89.90% for CD90, and 90.91% for CD105 protein expression were detected respectively as surface markers. On the other hand, it was found by flow cytometry experiments that hematopoietic stem cell surface markers used as negative control expressed 2.64% CD14, 1.44% CD31, 2.87% CD34 and 1.58% CD45, respectively.

In FIGS. 2A-2M, flow cytometry was applied for the characterization test of peMSC samples and average binding affinities of CD markers for n=5 cells from each group with standard deviation were given.

When the analyses of the CD surface markers in peMSCs were averaged, 75.52% for CD146, 73.99% for W5C5, 73.99% for PDGFR, 94.08% for CD44, 95.65% for CD29, 97.93% for Integrin β-1, 96.70% for CD73, 97.74% for CD90, and 87.43% for CD105 protein expression were determined, respectively. On the other hand, analysis of flow cytometry results showed that the expression of hematopoietic stem cell surface markers, used as negative control, was 1.40% for CD14, 1.20% for CD31, 1.60% for CD34 and 0.96% for CD45, respectively.

The mean values, standard deviations and "p significant" value ($****p\leq0.0001$) of markers for eMSCs isolated from endometrium samples taken from five healthy volunteers and endometriosis patients are given in Table 2.

TABLE 2

Mean percentage of stem cell markers in five different heMSC and peMSC and the value of $p \leq 0.0001$ was denoted as ****

| CD Markers | heMSC | | peMSC | | p Value |
|---|---|---|---|---|---|
| | % | ±SD | % | ±SD | |
| CD 146 | 42.74 | 3.08 | 75.52 | 2.49 | **** (p < 0.0001) |
| W5C5 | 44.6 | 2.36 | 73.99 | 6.29 | **** (p < 0.0001) |
| PDGFR | 43.38 | 4.1 | 73.99 | 2.29 | **** (p < 0.0001) |
| CD 44 | 92.03 | 4.29 | 94.08 | 4.07 | ns |
| CD 29 | 93.93 | 5.42 | 95.65 | 1.58 | ns |
| ITGβ-1 | 92.2 | 7.59 | 97.93 | 0.8 | ns |
| CD 73 | 91.86 | 6.1 | 96.7 | 2.02 | ns |
| CD 90 | 94.9 | 7.04 | 97.74 | 1.96 | ns |
| CD 105 | 90.91 | 5.67 | 87.43 | 3.65 | ns |
| CD 14 | 1.76 | 0.93 | 1.4 | 0.37 | ns |
| CD 31 | 1.13 | 0.49 | 1.2 | 0.19 | ns |
| CD 34 | 1.6 | 0.78 | 1.6 | 0.39 | ns |
| CD 45 | 1.41 | 0.34 | 0.96 | 0.4 | ns |

When the average values of the five different heMSC and peMSC given in Table 2 were taken into the account, it was found as a result of the flow cytometry experiments we have conducted that the expression of surface markers CD 146, W5C5 and PDGFR were significantly (****, $p<0.0001$) higher in peMSC samples isolated from patients diagnosed with endometriosis compared to the heMSC samples. In peMSC, the expression of CD 146 was 1.77 times, the expression of W5C5 was 1.65 times and the expression of PDGFR was 1.71 times higher compared to heMSCs. In this context, our experiments have shown that CD146, W5C5 and PDFGR are synthesized more in patient cell samples than in healthy cells, and that these biomarkers will be a biomarker for the diagnosis of endometriosis when used individually or in combination.

Within the scope of our invention, Western blot method was used to determine the amount of TG2 in total protein isolated from control (healthy) and patient MSCs. For this purpose, protein isolated from five different control samples and five different patient samples was separated by poly-acrylamide gel electrophoresis (SDS-PAGE) technique and after being transferred to nitrocellulose membrane by Western Blot technique. In FIGS. 3A-3C, TG2 protein expression levels were determined using the antibody recognizing TG2 while j-actin antibody was used in the whole Western Blot technique to ensure equal amount of protein loading.

In FIGS. 3A-3C, it was observed that TG2 levels in peMSC lysates isolated from five different patients were higher than those in heMSC lysates isolated from healthy individuals. When the TG2 protein levels in cells isolated from healthy individuals and patients were compared between the groups respectively, it was observed that the TG2 level in the patient cells in group-1 was 7.4 times higher than the healthy cells. It was detected that the patients in group 2 had TG2 protein level 6.1 times higher than the healthy individuals. Similar results were observed in protein samples of patient cells in group 3, group 4 and group 5, and it was detected by Image J analyses that endometriosis patients had 6.5, 6.3 and 5.8 times more TG2 protein respectively, when compared to healthy samples. In FIG. 3C, the mean value of the TG2 protein level of all groups is presented and statistical results in FIG. 3C were evaluated with the Oneway Anova test in GraphPad Prism 6. As a result of the statistical analysis, $p<0.0001$ value was obtained, and the result was depicted with ****. FIG. 3C shows the mean value of the TG2 protein level of all groups, it was determined that the average TG2 protein level of the peMSC samples was 4.7 times higher than that of the heMSC samples.

In order to prove our hypothesis that increased CD146, PDGFR and W5C5 in peMSC samples might be TG2-driven, which increases the originality of our invention, we performed voluntary/controlled TG2 silencing by using shRNA technology in this part of our study. Experimental samples consisted of untreated heMSCs, scrambled shRNA-treated heMSCs (heMSC+SCR) and peMSCs (peMSC+SCR), and finally, TG2-targeting shRNA-treated peMSCs (peMSC+shRNA). First, in order to prove that the silencing of TG2 in a voluntary and controlled manner by using shRNA technology is carried out successfully, Western Blot (FIGS. 4A-4C) and RT-PCR methods were applied to heMSC, heMSC+SCR, peMSC, peMSC+SCR and peMSC+shRNA samples.

Figure 4A:
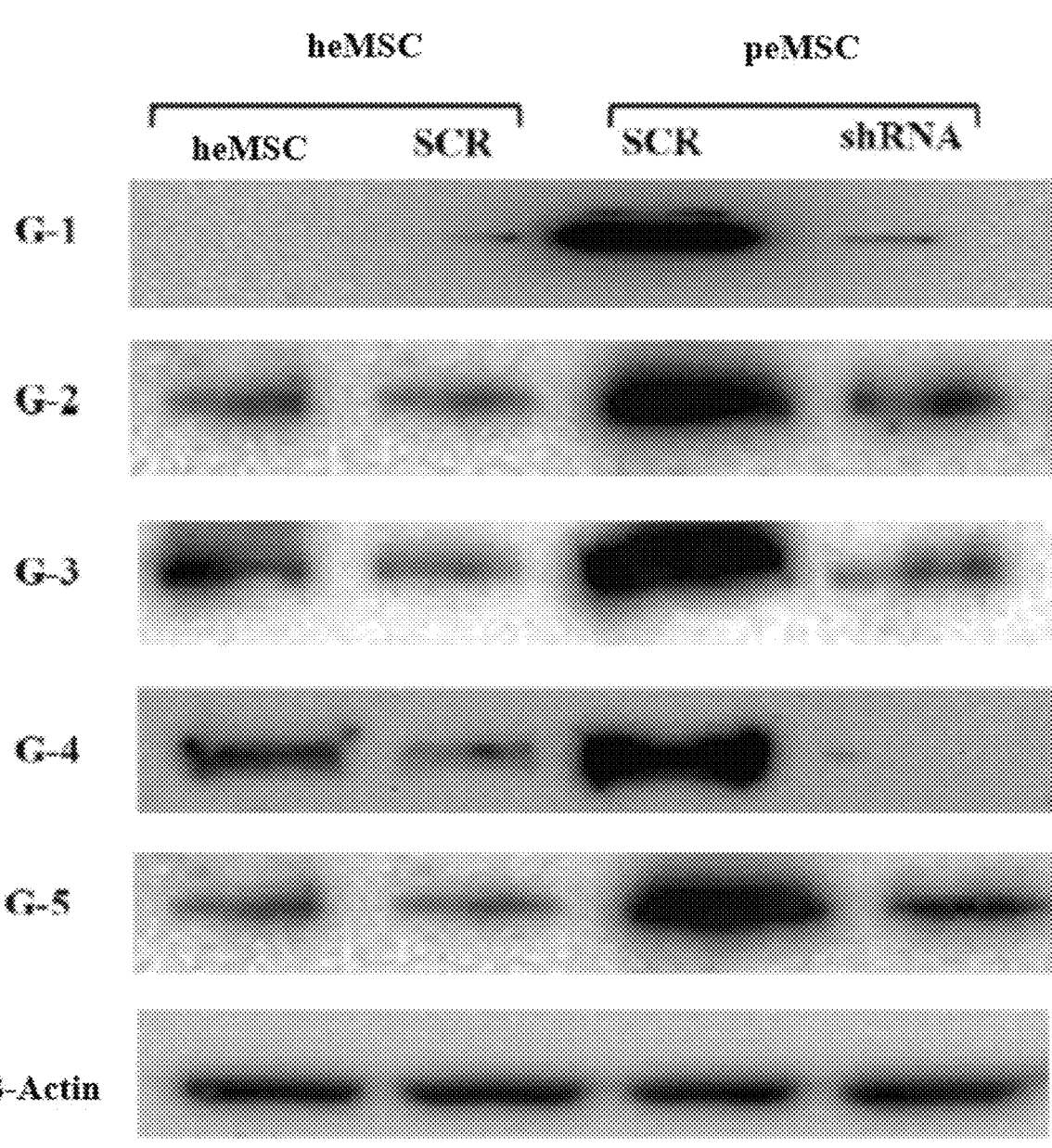
FIGS. 4A-4C show the western Blot results showing the protein levels of TG2 silenced by shRNA technique in all isolated eMSCs. Where

In FIG. 4A, changes in TG2 protein levels in cells after TG2-targeted shRNA application were determined by measuring band intensities on the membrane after Western blot technique. The quantitative results of these band intensities were detected by using the Image J software program and are presented in the graph in FIG. 4B. According to these results, SCR shRNA transduction in all groups (n=5) for heMSC did not cause any change in TG2 expression (FIG. 4C) While the transduction of peMSCs with viral particles carrying TG2-targeting shRNA caused a 1.62-fold decrease in Group 1, this value was determined as 1.62-fold for Group 2, 3.1-fold for Group 3, 3-fold for Group 4 and 2.37-fold for Group 5. TG2 protein expression measured as a result of reduction of TG2 expression with shRNA (peMSC+shRNA) in peMSC was found to be similar when compared to heMSC and heMSC+SCR (FIG. 4C). Statistical analysis showed that there was no significant difference between them and it was represented as "ns" in the graph. A similar comparison was made between the heMSC samples and the peMSC samples on the same graph, as a result, it was observed that peMSC synthesized 2.6 times more TG2 than peMSC+shRNA and significant $p<0.00001$ value is indicated by *****.

After successful silencing of TG2 with shRNA, flow cytometry experiments were performed again to detect CD146, PDGFR, and W5C5 surface markers in five different healthy and endometriosis eMSCs, and our results comparing the heMSC and heMSC+SCR samples are given in FIGS. 5A-5M, and our results comparing the peMSC+SCR and peMSC+shRNA SCR samples are given in FIGS. 6A-6M.

In the flow cytometry results, it was observed that control samples treated with the scrambled virus particle (heMSC+SCR) had similar values compared to the heMSC samples. Result for statistical analysis of the mean values of heMSC and heMSC+SCR samples are presented in Table 3.

TABLE 3

Mean percentage of stem cell markers in five different
heMSC and heMSC + SCR samples and the p value
with no statistical difference shown by "ns"

| CD Markers | heMSC | | heMSC + SCR | | |
| | % | ±SD | % | ±SD | p Value |
| --- | --- | --- | --- | --- | --- |
| CD 146 | 46.15 | 3.2 | 45.89 | 3.14 | ns |
| W5C5 | 44.89 | 4.05 | 45.22 | 3.66 | ns |
| PDGFR | 43.05 | 3.01 | 42.93 | 4.15 | ns |
| CD 44 | 89.38 | 5.16 | 90.49 | 5.31 | ns |

TABLE 3-continued

Mean percentage of stem cell markers in five different
heMSC and heMSC + SCR samples and the p value
with no statistical difference shown by "ns"

| CD Markers | heMSC | | heMSC + SCR | | |
| | % | ±SD | % | ±SD | p Value |
| --- | --- | --- | --- | --- | --- |
| CD 29 | 92.58 | 4.5 | 91.27 | 5.77 | ns |
| ITGβ-1 | 94.2 | 2.79 | 94.12 | 2.91 | ns |
| CD 73 | 94.37 | 4.76 | 94.69 | 4.65 | ns |
| CD 90 | 92.69 | 1.76 | 91.15 | 1.22 | ns |
| CD 105 | 90.78 | 6.43 | 91.56 | 6.54 | ns |
| CD 14 | 2.18 | 1.06 | 1.94 | 1.09 | ns |
| CD 31 | 1.69 | 0.91 | 1.6 | 0.78 | ns |
| CD 34 | 2.12 | 0.76 | 2.09 | 0.95 | ns |
| CD 45 | 1.33 | 0.53 | 0.89 | 0.24 | ns |

According to the results in Table 3, it has been proved by the experiments we conducted within the framework of our invention that the lentivirus we use as a carrier has no effect on the cells.

In this part of our results, in order to show that increased CD146, PDGFR and W5C5 in peMSC samples may be TG2-driven, flow cytometry method was applied to peMSC+SCR samples treated with scrambled control lentiviral particles and peMSC+shRNA samples treated with tTG-targeting shRNA and the results are given in FIGS. 6A-6M.

Flow cytometry results set forth that peMSC+SCR cell surface markers were similar to peMSC cells. In TG2-targeting shRNA-treated peMSC+shRNA cells, expressions of CD146, W5C5 and PDGFR surface markers, which are highly contained in peMSCs, is decreased to the levels seen in healthy eMSCs in response to TG2 silencing. The results of the statistical analysis of the mean values of peMSC+SCR and peMSC+shRNA samples are presented in Table 4.

TABLE 4

Mean percentage of stem cell markers in five different
peMSC and peMSC + shRNA samples and p value with
statistical difference (p < 0.0001) shown by "***"

| CD Markers | peMSC + SCR | | peMSC + shRNA | | |
| | % | ±SD | % | ±SD | p Value |
| --- | --- | --- | --- | --- | --- |
| CD 146 | 71.43 | 5.1 | 35.54 | 5.37 | **** (p < 0.0001) |
| W5C5 | 76.63 | 2.49 | 42.09 | 3.43 | **** (p < 0.0001) |
| PDGFR | 78.54 | 0.5 | 34.8 | 4.04 | **** (p < 0.0001) |
| CD 44 | 89.06 | 6.57 | 90.13 | 7.64 | ns |
| CD 29 | 92.47 | 3.26 | 93.31 | 5.55 | ns |
| ITGβ-1 | 93.59 | 3.55 | 93.7 | 3.4 | ns |
| CD 73 | 90.84 | 6.75 | 89.65 | 7.36 | ns |
| CD 90 | 88.21 | 7.26 | 87.86 | 8.17 | ns |
| CD 105 | 92.97 | 5.36 | 95.77 | 4.51 | ns |
| CD 14 | 1.74 | 0.67 | 1.92 | 0.88 | ns |
| CD 31 | 1.66 | 0.4 | 2 | 0.26 | ns |
| CD 34 | 1.96 | 0.89 | 2.02 | 0.91 | ns |
| CD 45 | 1.72 | 0.36 | 1.67 | 0.27 | ns |

Considering the results in Table 4, when peMSC+SCR samples were compared with peMSC+shRNA samples, in peMSC+shRNA samples treated with TG2-targeting shRNA, statistically, an expression reduction (****, p<0.0001) of 2.1-fold for CD146, 1.82-fold for W5C5 and 2.26-fold PDGFR was observed, respectively. These results for the first time in the literature constitute a proof that increase in CD146, PDGFR and W5C5 expression levels in peMSC samples seen in the development of endometriosis is TG2-driven.

Figure 7:
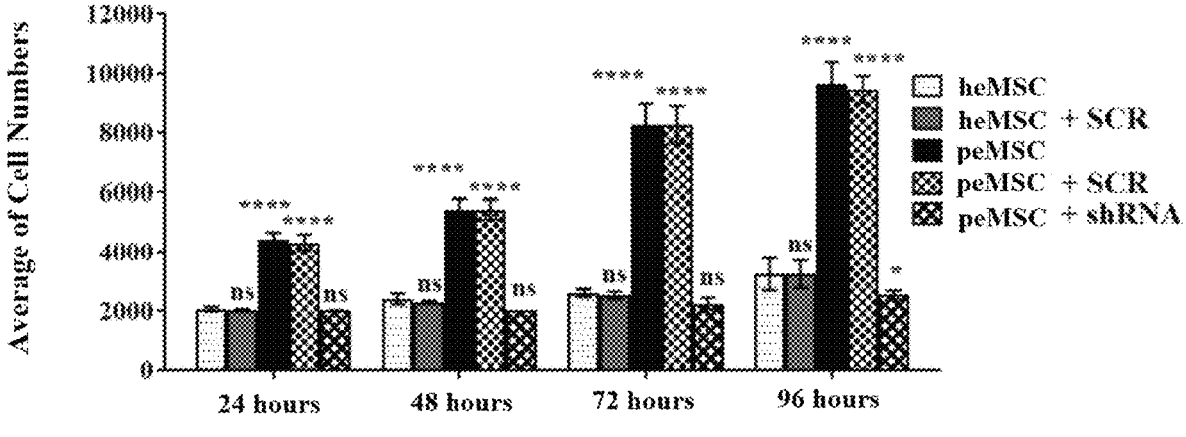
FIG. 7 shows the effect of voluntary and controlled silencing of tTG2 with shRNA on mean cell growth of eMSC samples in five different groups. "ns" was used for the non-significant p value of the statistical analysis results, and *p<0.05, ****p<0.00001, respectively, were used for the significant values.
Figures 8A, 8B:
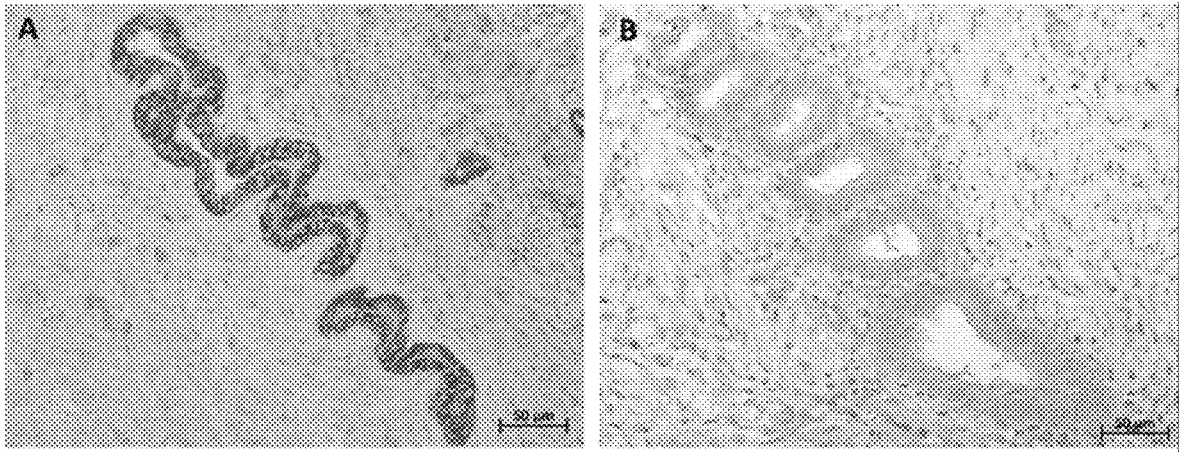
FIGS. 8A-8D show representative images for the immunohistochemical staining with surface markers specific to endometrium of the tissue sections taken from endometriosis foci. Images showing CD146 (FIG. 8A), integrin β-1 (FIG. 8B), PDGFR (FIG. 8C) and TG2 (FIG. 8D) markers. Scale bar: 50 μm.
Figures 8C, 8D:
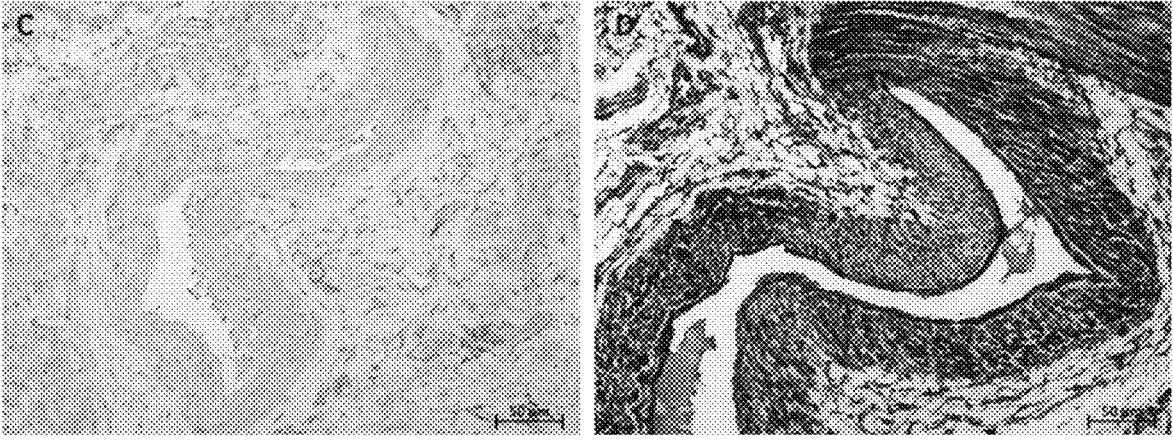

For the comparative detection of TG2-driven cell proliferation in peMSCs, WST-1 assay was applied to the samples of heMSC, heMSC+SCR, peMSC, peMSC+SCR and peMSC+shRNA at different time points for 24, 48, 72 and 96 hours and the results are given in FIG. 7.

According to the results in FIG. 7, it was set forth that at the end of 24, 48, 72 and 96 hours, heMSC and heMSC+SCR cells proliferated more slowly than peMSC and peMSC+SCR cells. At the end of 24 and 48 hours, it was observed that peMSC and peMSC+SCR samples with high TG2 expression had an average of 2.1 and 2.3 times more cells compared to heMSCs, and at the end of 72 and 96 hours, this rate was 3.2 and 3.0 times higher, respectively. In peMSC+shRNA cell samples in which TG2 expression was silenced, it was detected that the mean cell number was similar to that of heMSC and heMSC+SCR cells ($p>0.05$).

After performing immunohistochemical staining on the tissues taken from endometriosis foci with TG2, CD146, PGDGR, SUSD2 (W5C5) and Integrin β-1 antibodies, Tissue sample was probed separately for each antibody and five images each were taken from different regions with the 40× lens using the light module of the Zeiss fluorescence microscope. Representative images for each antibody are illustrated in FIGS. 8A-8D. In all samples, it was detected that Integrin β-1, TG2, CD146 and PGDGR markers are expressed more intensely in the glands of the endometriosis focus than in the stromas. No staining for the SUSD2 (W5C5) antibody was observed in any of the endometriosis focal tissue samples.

reliable diagnostic test with fast results, causes an average of 7-11 years delay in diagnosis for women with endometriosis [84], [85].

In the light of this information in the literature, in our invention, in which we have started to work on a high-sensitivity diagnostic test, we have discovered that TG2, which can be a novel biological marker for the diagnosis of endometriosis and which is both cost-effective and provides the possibility of "application/result" in a short time without the need for surgical intervention, can be used in the diagnosis of endometriosis by driving endometrial MSCs-specific CD146, W5C5 and PDFGR expression. In this context, the importance of TG2 in both the diagnosis and development of endometriosis was demonstrated for the first time in the literature by the experiments we conducted within the scope of our invention.

In the flow cytometric examination, it was proved that the cells isolated from the endometrium of healthy (FIGS. 1A-1M) individuals and patients (FIGS. 2A-2M) have mesenchymal stem cell character that is compatible with the eMSC characterization information in the literature [86], [87], [88], [89]. On the other hand, these results indicate that the endometrium is a high source of mesenchymal stem cells and that mesenchymal stem cells localized in the endometrium contribute to the repetition of the menstrual cycle, the repair of the endometrium and ensuring its dynamic structure [90], [91]. It was determined by flow cytometry in the same cell groups that CD146, W5C5 and PDFGR [92] markers specific for endometrial mesenchymal stem cells,

TABLE 5

Expression levels of CD146, ITGβ-1, PDGFR and TG2 markers in the stroma and glands of the studied endometriosis focal tissues are given in percentage.

|  | CD 146 | | ITGB1 | | PDGFR | | TG2 | |
|---|---|---|---|---|---|---|---|---|
|  | Gland | Stroma | Gland | Stroma | Gland | Stroma | Gland | Stroma |
| 0 | 11.8 | 58.8 | 23.5 | 35.3 | 17.6 | 11.8 | 0.0 | 41.2 |
| + | 11.8 | 17.6 | 17.6 | 11.8 | 23.5 | 47.1 | 47.1 | 11.8 |
| ++ | 29.4 | 23.5 | 52.9 | 47.1 | 17.6 | 17.6 | 17.6 | 23.5 |
| +++ | 47.1 | 0.0 | 5.9 | 5.9 | 41.2 | 23.5 | 35.3 | 23.5 |

It was detected that in the glands of all studied endometriosis focal tissues, CD146, PDGFR and TG2 markers were expressed more than 50% as intense (++) or very intense (+++) (Table 5).

Results and Application of the Invention

As mentioned in previous studies, endometriosis is the condition in which endometrial tissue, which should be in the uterus, is also present outside of the uterus, most commonly on the surface of the abdominal cavity, in the ovaries, or in much more distant regions such as the brain [78]. When the prevalence among women was examined in general, it was determined as 6%-10% [79], [80], [81]. However, it has been shown that the detection rate of endometriosis disease is between 35-50% in women with pelvic pain or infertility [79], [80], [81]. The result of the US cost report for endometriosis diagnosis is $69.4 million per year [82]. "Laparoscopy" constitutes a large part of this expensive diagnosis [82]. Although laparoscopy is an important diagnostic method for the diagnosis of endometriosis, it includes surgical risks such as surgical problems that may arise during the operation, intestinal and bladder damage, damage to the ovary, damage to large vessels and bleeding, as well as high cost and long-term patient resting process [6], [82], [83]. The absence of a non-invasive easy to apply, are more expressed in patient cell samples compared to healthy cells. Increased expression of CD146, W5C5, and PDFGR [92], which are specific to endometrial-derived mesenchymal stem cells, in patient endometriotic cells may have conferred cell migration, adhesion and invasion potential to peMSC samples. Since the amounts of CD146, PDGFR and W5C5, which are known to play a role in cell migration, adhesion and invasion, are high in patient cells and PDGFR cooperates directly with TG2, it is considered that increase in CD146, PDGFR and W5C5 in peMSC samples might be TG2-driven. In the previous study by Zemskov et al., it has been shown in different cell samples that cell surface TG2 interacts with PDGFR and triggers TG2-driven PDGFR-dependent cell adhesion with integrins [93], [94]. On the other hand, in recent studies conducted with central nervous system cells, it has been shown that CD146 plays an essential role in PDGFR-β-mediated signal transduction and triggers cell migration and adhesion by PDGFR-β phosphorylation as a result of CD146 dimerization [95]. Although the relationship between CD146 and PDGFR was explained in this study, their relationship with TG2 and roles in endometriosis were not elucidated. In accordance with the flow cytometry results, the presence of TG2 was investigated in heMSC and peMSC samples to determine the role of TG2 in the increased expression of CD146, PDGFR and W5C5 in peMSC samples. With Western Blot (FIGS. 3A-3C) and RT-PCR experiments conducted in this context, protein content and gene expression of TG2 were investigated in heMSC and peMSC samples and it was detected that both protein and gene expression of TG2 was higher in patient samples compared to controls.

Figure 4B:
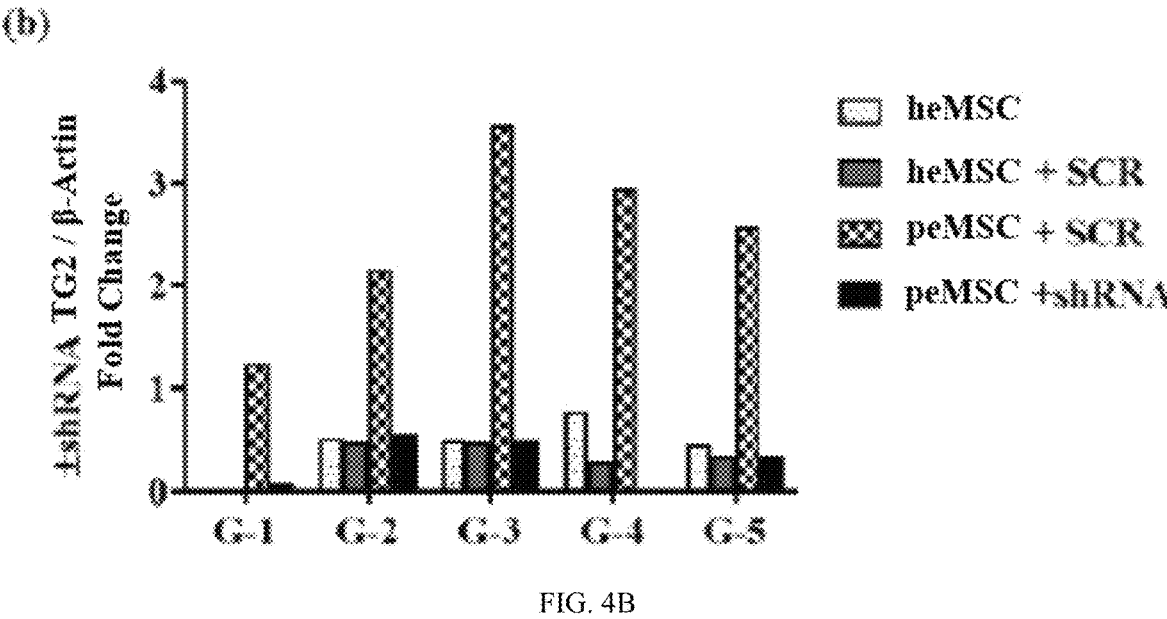
Figure 4C:
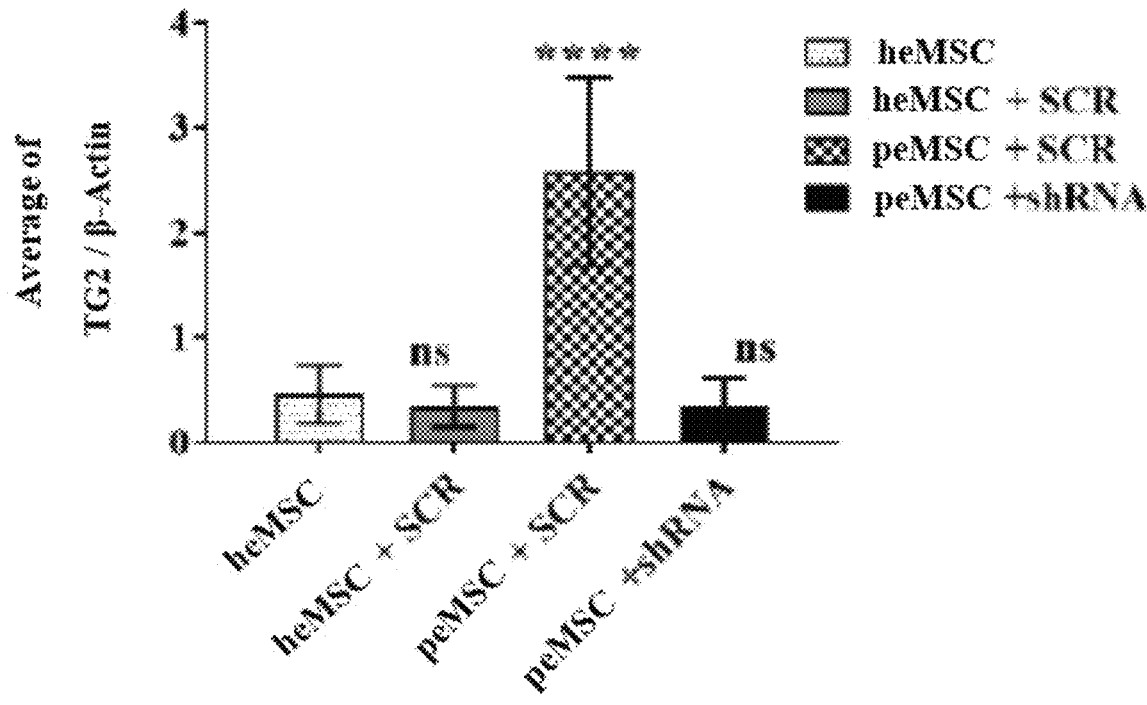
Figures 5J, 5K:
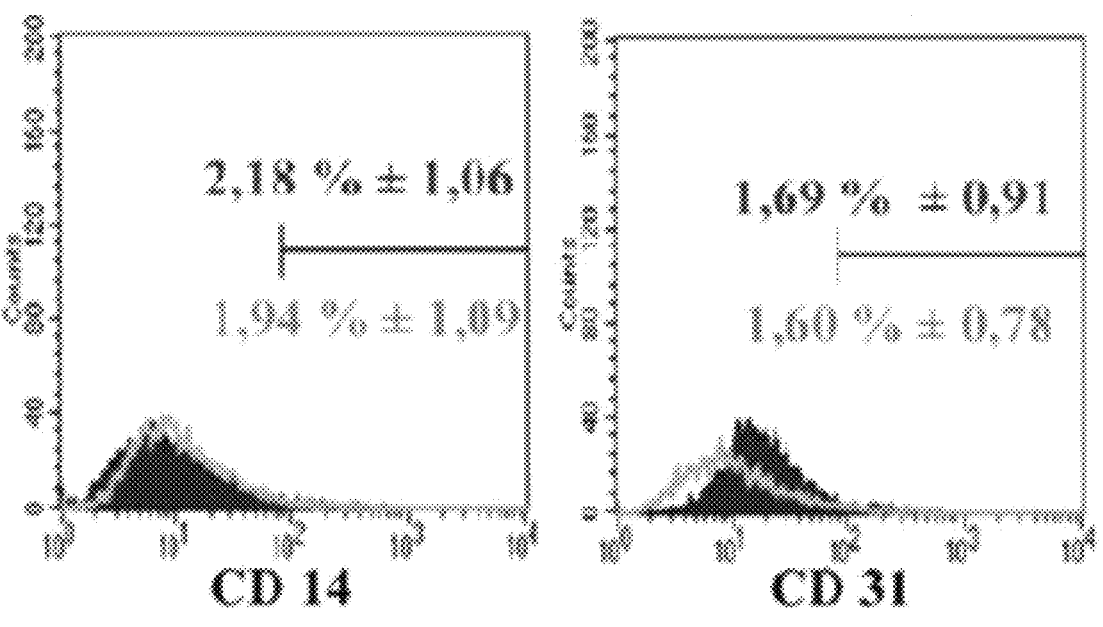
Figures 5L, 5M:
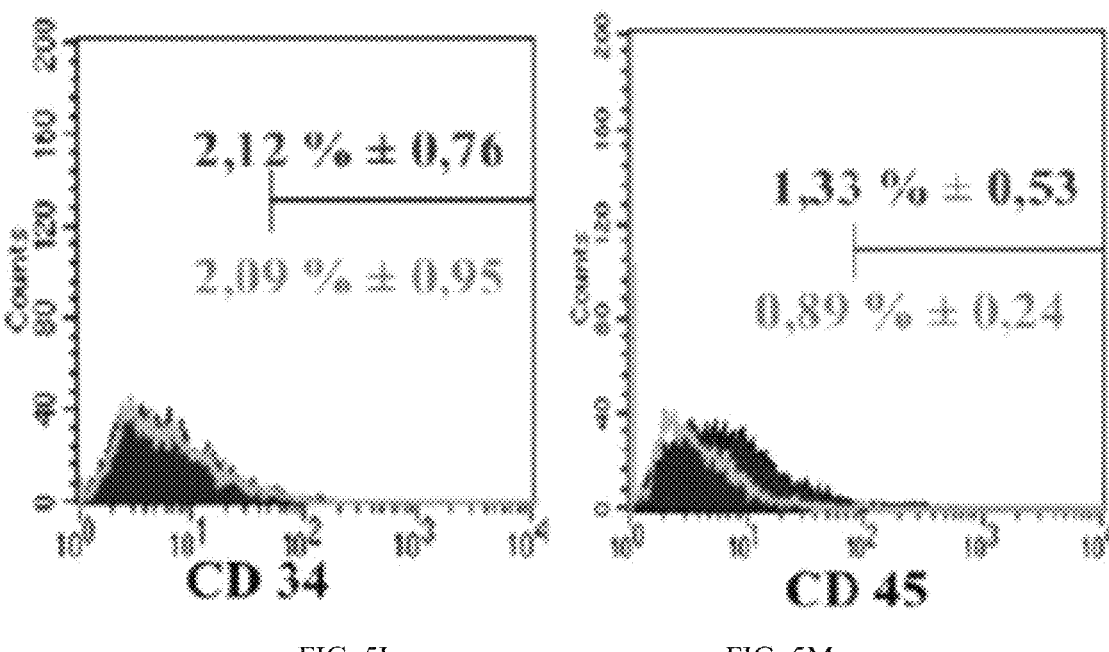
Figures 6F, 6G, 6H, 6I:
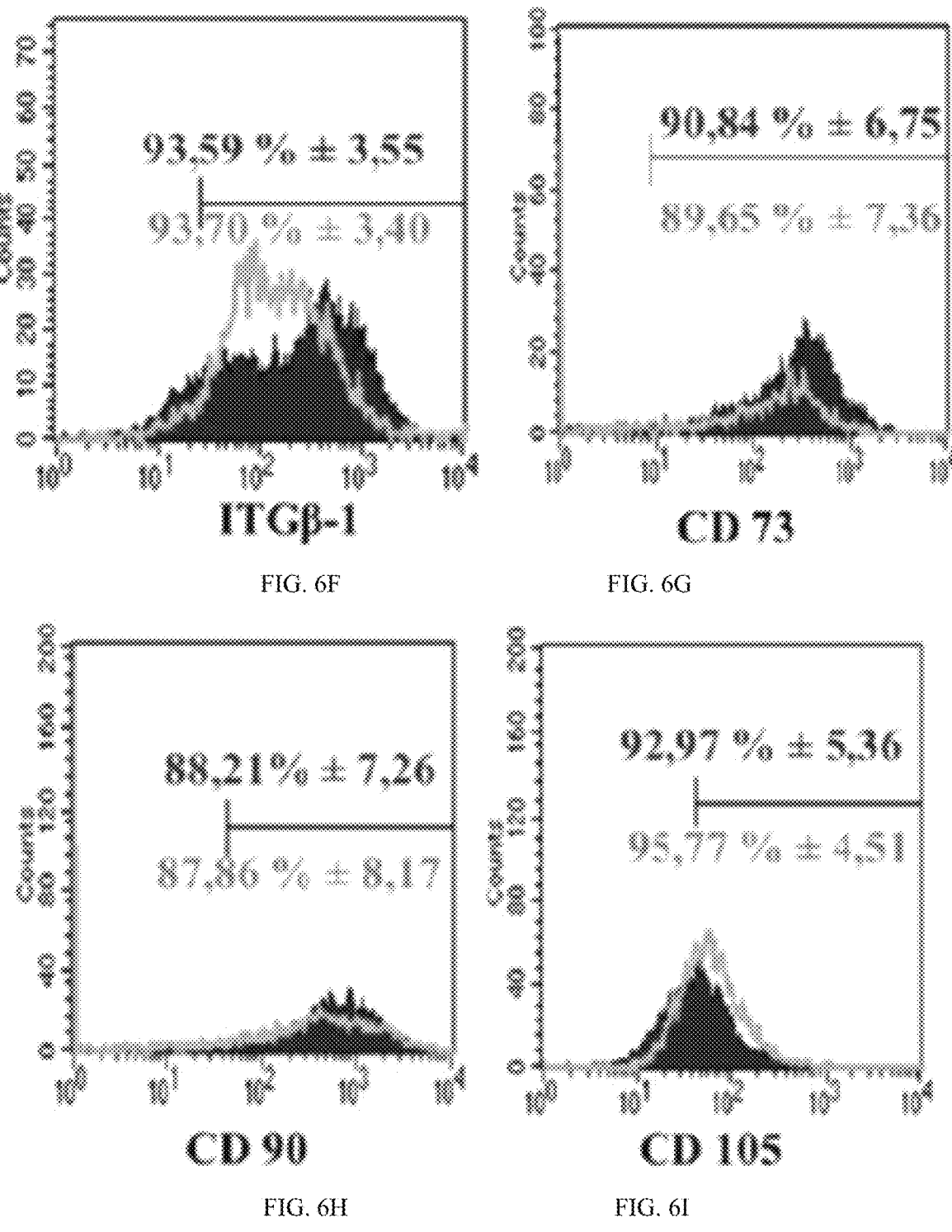
Figures 6J, 6K, 6L, 6M:
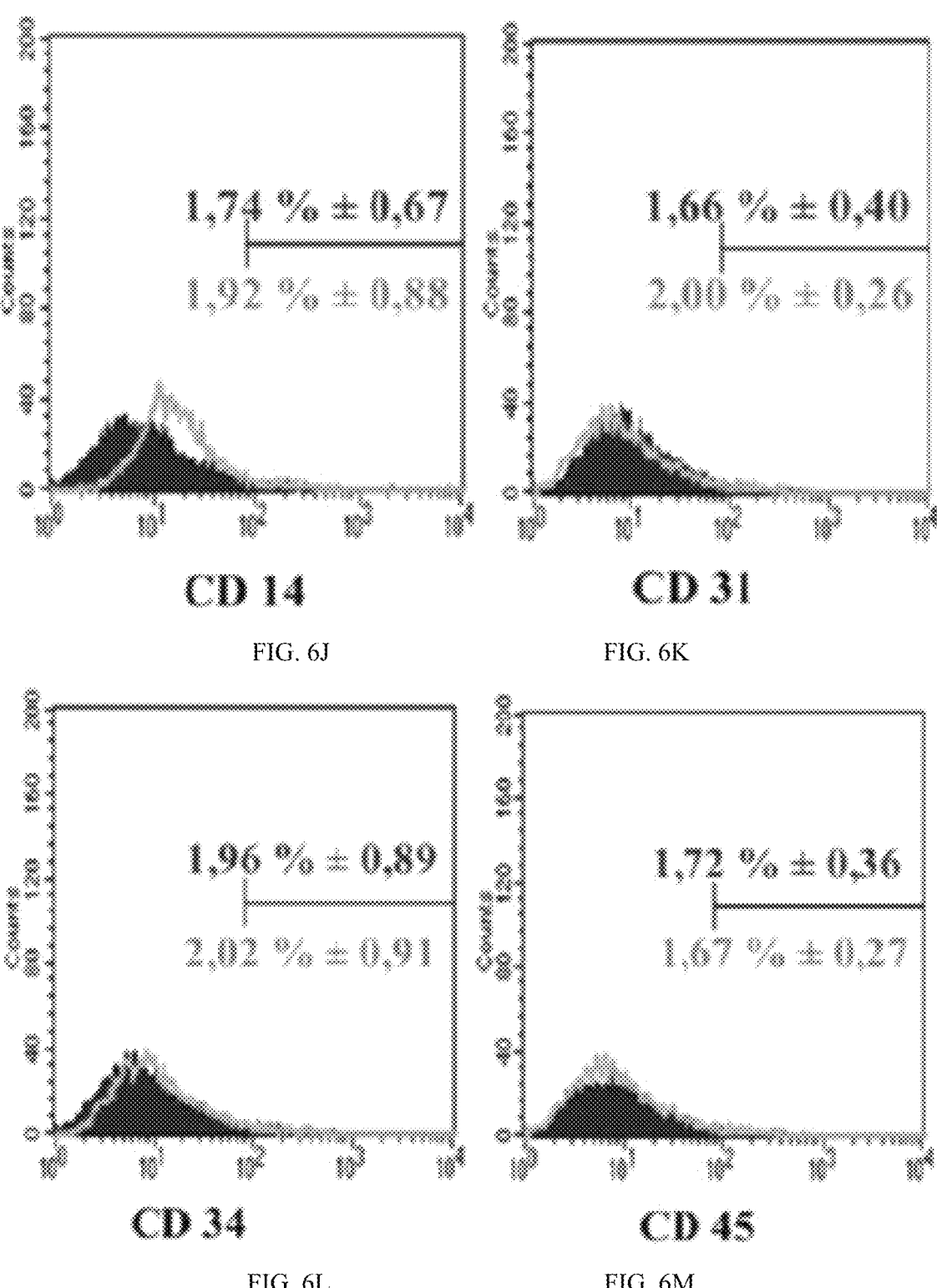

As shown with data presented so far that prove our hypothesis, to understand whether the increased CD146, PDGFR and W5C5 surface markers in peMSCs are under the control of TG2 expression, TG2 expression was silenced in a voluntary and controlled manner by applying shRNA technology to eMSCs (FIGS. 4A-4C). While it was observed that the level of TG2 protein (FIGS. 4A-4C) was reduced after applying shRNA to peMSCs, (scrambled) shRNA containing control lentiviral particles applied to peMSCs and heMSCs did not reduce the TG2 protein level. As also disclosed in the literature, while shRNAs inhibit proteins that are products of the target gene, the scrambled comprising control lentiviral particles comprises about 19-25 nucleotide sequences in the human genome that do not correspond to any cellular message, no changes are expected in cells treated with the scrambled [96], and this information is parallel with our results. With the successful application of shRNA in peMSC samples that synthesize and express TG2 at a high level, the role of TG2 in endometriosis was molecularly elucidated by us through detection of changes in CD146, PDGFR and W5C5 surface markers, the proliferative potential of cells, their capacity to migrate to regions outside the uterus, and their ability of invasion in new places where they have migrated.

As known, in addition to its $Ca^{+2}$-dependent cross-enzyme activity [41], [46], [97], [98], [99], TG2 can lose its cross-linking activity independently of $Ca^{+2}$ and bind to and hydrolyze GTP, and take an active role in cell adhesion and migration as a G protein [41], [45], [36], [50], [52]. In the light of this information in the literature and as a result of the experiment we presented within the scope of our invention, it has been investigated whether peMSCs have gained the ability to migrate to regions outside the uterus and to adhere to and invade the said regions, by means of the high level of TG2 expression they contain.

According to the results we presented in FIGS. 4A-4C, following controlled and voluntary silencing of TG2 with shRNA, CD146, W5C5 and PDGFR surface markers in peMSC+shRNA cells were reduced to the levels observed in heMSC, heMSC+SCR cells (FIGS. 6A-6M, Table 3 and Table 4). These results show us that the surface markers of CD146, W5C5 and PDFGR, which are highly expressed in peMSC cells, are under the control of TG2 gene expression.

WST-1 assays, which are performed at $24^{th}$, $48^{th}$, $72^{nd}$ and $96^{th}$ hours for determining the effect of TG2 expression on eMSC cell proliferation (FIG. 7) showed that peMSC cells proliferated 1.3 times faster when compared to heMSC samples. With TG2 silencing, the proliferative capacity of peMSC+shRNA cells was reduced to the level of healthy heMSC levels. These results constitute a proof that cell proliferation in endometriosis is performed under the control of TG2.

In addition to our studies with CD146, Integrin β-1, PDGFR, TG2 and W5C5 markers in endometrial MSCs, the expression levels in the endometriosis foci taken from different regions of 17 patients in different stages of endometriosis were also examined by immunohisto-biochemical staining method. Stainings in glands and stroma in tissues were evaluated separately. Results showed that as we have shown in eMSCs in the glands of all endometriosis focal tissues, CD146, PDGFR and TG2 markers were expressed more than 50% as intense (++) or very intense (+++) (Table 5). It was detected that CD146, PDGFR and TG2 expression in the stroma were lower than that in the glands in the endometriosis focal tissues (FIG. 8A-8D). Although Integrin β-1 expression, which did not show an increase in eMSCs, was expressed in endometriosis focal tissues, no change in expression was detected in eMSCs isolated from healthy individuals and patients. This suggests that Integrin β-1 expression is increased during eMSCs endometriosis focus formation. Our immunohistochemistry studies conducted with W5C5 within the framework of the present patent application demonstrated for the first time in the literature that, contrary to Gargett et al., the expression of W5C5 was suppressed in the endometriosis focal tissue, while this marker was increased in eMS cells isolated from endometriosis patient endometrium.

Within the framework of the studies conducted according to the present application, the use of TG2, CD146, PGDGR, SUSD2 (W5C5) and Integrin β-1 markers alone or in combination as a biomarker in the diagnosis of endometriosis is requested to be patented.

REFERENCES

[1]. Rokitansky, C. 1860. "Über Uterusdrüsen-Neubil-dung in Uterus-und Ovarial-Sarcomen. (On the neoplasm of uterus glands on uterine and ovarian sarcomas)", Zeitschr Ges Aerzte Wien 16(1) 577-581.

[2]. Sampson J A: Peritoneal endometriosis due to the menstrual dissemination of endometrial tissue into the peritoneal cavity. Am J Obstet Gynecol 1927; 14: 422-469.

[3]. Cramer D W, Missmer S A. The epidemiology of endometriosis. Ann N Y Acad Sci 2002; 955:11-22.

[4]. Tietjen G E, Bushnell C D, Herial N A, Utley C, White L, Hafeez F. Endometriosis is associated with prevalence of comorbid conditions in migraine. Headache 2007; 47:1069-78.

[5]. Pasoto S G, Abrao M S, Viana V S, Bueno C, Leon E P, Bonfa E. Endometriosis and systemic lupus erythematosus: a comparative evaluation of clinical manifestations and serological autoimmune phenomena. Am J Reprod Immunol 2005; 53:85-93.

[6]. Sinaii N, Cleary S D, Ballweg M L, Nieman L K, Stratton P. High rates of autoimmune and endocrine disorders, fibromyalgia, chronic fatigue syndrome and atopic diseases among women with endometriosis: a survey analysis. Hum Reprod 2002; 17:2715-24.

[7]. Lamb K, Nichols T R. Endometriosis: a comparison of associated disease histories. Am J Prev Med 1986; 2:324-9.

[8]. Mao A J, Anastasi J K. Diagnosis And Management Of Endometriosis: The Role Of The Advanced Practice Nurse In Primary Care. Journal of the American Academy of Nurse Practitioners 2010; 22: 109-116.

[9]. Somigliana E, Vercellini P, Vigano P, Benaglia L, Crosignani P G, Fedele L. Non-invasive diagnosis of endometriosis: the goal or own goal? Hum Reprod 2010; 25:1863-8.

[10]. Matsuzaki S, Houlle C, Darcha C, Pouly J L, Mage G, Canis M. Analysis of risk factors for the removal of normal ovarian tissue during laparoscopic cystectomy for ovarian endometriosis. Hum Reprod 2009; 24:1402-6.

[11]. Zanelotti A, Decherney A H. Surgery and Endometriosis. Clin Obstet Gynecol. 2017; 60(3):477-484.

[12]. Kitawaki J, Ishihara H, Koshiba H, et al. Usefulness and limits of CA-125 in diagnosis of endometriosis without associated ovarian endometriomas. Hum Reprod 2005; 20:1999-2003.

[13]. Eskenazl B., Warner M. L., 1997. "Epidemiology of endometriosis". Obstet Gynecol Clin North Am; 24:235-58.

[14]. Vercellini, P., Vigano, P., Somigliana, E., & Fedele, L. (2014). Endometriosis: pathogenesis and treatment. Nature Reviews Endocrinology, 10(5), 261.

[15]. Sampson J. A., 1922. "Ovarian hematomas of endometrial type (perforating hemorrhagic cysts of the ovary) and implantation adenomas of endometrial type". Boston Med Surg J; 186:445-473.

[16]. Vignali M., Infantino M., Matrone R., et al. 2002. "Endometriosis: novel etiopathogenetic concepts and clinical perspectives." Fertil Steril; 78:665-78.

[17]. Vinatier D., Dufour P., Oosterlynck D., 1996. "Immunological aspects of endometriosis." Hum Reprod Update; 2: 371-84.

[18]. Matarese G., De Placido G., Nikas Y., Alviggi C., 2003. "Pathogenesis of endometriosis: natural immunity dysfunction or autoimmune disease?". Trends Mol Med; 9: 223-28.

[19]. Kyama C. M., Debrock S., Mwenda J. M., D'Hooghe T. M., 2003. "Potential involvement of the immune system in the development of endometriosis". Reprod Biol Endocrinol; 1: 123.

[20]. Barrier B. F., Kendall B. S., Ryan C. E., Sharpe-Timms K. L., 2006. "HLA-G is expressed by the glandular epithelium of peritoneal endometriosis but not in eutopic endometrium". Hum Reprod; 21: 864-69.

[21]. Somigliana E., Vercellini P., Gattei U., et al. 2007. "Bladder endometriosis: getting closer and closer to the unifying metastatic hypothesis". Fertil Steril; 87:1287-90.

[22]. Di W., Guo S. W., 2007. "The search for genetic variants predisposing women to endometriosis". Curr Opin Obstet Gynecol; 19:395-401.

[23]. Kashima K., Ishimaru T., Okamura H., et al. Familial risk among Japanese patients with endometriosis. Int J Gynaecol Obstet 2004; 84:61-64.

[24]. Ryer S., Foster W., 2002. "Environmental dioxins and endometriosis". Toxicological Sciences; 70:161-70.

[25]. Collins F. S., McKusick V. A., 2001. "Implications of the Human Genome Project for medical science". Jama; 285:540-4.

[26]. Kleeman S. D., Silva W. A., 2002. "Gynecologic anatomy. In: Sokol A I, Sokol E R, eds. The Requisites in Obstetrics and Gynecology". General Gynecology. Philadelphia, Mosby-Elsevier, 2007:87.

[27]. Starzinkski Powitz A., Zeitvogel A., Schreiner A., et al. 2001. "In search of pathogenic mechanisms in endometriosis: the challenge for molecular cell biology". Curr Molec Med; 1: 655-64.

[28]. Gargett C. E. 2007. "Uterine stem cells: what is the evidence?". Hum Reprod Update; 13: 87-101.

[29]. Leyendecker G., Herbertz M., Kunz G., et al. 2002. "Endometriosis results from the dislocation of basal endometrium". Human Reprod; 17: 2725-36.

[30]. Sasson I. E., Taylor H. S., 2008. "Stem Cells and the Pathogenesis of Endometriosis". Ann NY Acad Sci; 1127: 106-15.

[31]. Fazleabas A. T., Brudney A., Gurates B., et al. 2002. "A modified baboon model for endometriosis". Ann N Y Acad Sci; 955: 308-17.

[32]. Akimov S. S., Krylov D, Fleischman L F, Belkin A M. 2000 "Tissue transglutaminase is an integrin-binding adhesion coreceptor for fibronectin". J Cell Biol. 148(4): 825-38.

[33]. Gaudry C. A., Verderio E., Aeschlimann D., Cox A., Smith C., Griffin, M., 1999. "Cell surface localization of tissue transglutaminase is dependent on a fibronectin-binding site in its N-terminal beta-sandwich domain". J. Cell Biol., 274, 30707-14.

[34]. Telci D., Wang Z., Li X., Verderio E. A., Humphries M. J., Baccarini M., Basaga H., Griffin M., 2008. "Fibronectin-Tissue Transglutaminase Matrix Rescues RGD-impaired Cell Adhesion through Syndecan-4 and β1 Integrin Co-signaling." J Biol Chem 283, 20937-2.

[35]. Wang Z., Collighan R. J., Gross S. R., Danen E. H. J., Orend G., Telci D., Griffin M., 2010. "RGD-independent Cell Adhesion via a Tissue Transglutaminase-Fibronectin Matrix Promotes Fibronectin Fibril Deposition and Requires Syndecan-4/2 and α5β1 Integrin Co—.

[36]. Kao, A. P., Wang, K. H., Chang, C. C., Lee, J. N., Long, C. Y., Chen, H. S., . . . & Tsai, E. M. (2011). Comparative study of human eutopic and ectopic endometrial mesenchymal stem cells and the development of an in vivo endometriotic invasion model. Fertil.

[37]. Viganq P., Parazzini F., Somigliana E, et al. 2004. "Endometriosis: epidemiology and aetiological factors." Best Pract Res Clin Obstet Gynaecol; 18:177-200.

[38]. Masuda H, Anwar S S, Buhring H J, Rao J R, Gargett C E. 2012. "A novel marker of human endometrial mesenchymal stem-like cells". Cell Transplant. 21:2201-2214.

[39]. Kurt I., Batukan, M. Attar, R., Telci, D. 2016. "Does tissue transglutaminase have a role in the development of endometriosis?". Febs Journal Volume: 283 Pages: 119.

[40]. Iismaa S. E., Chung L., Wu M J., Teller D. C., Yee V. C., Graham R. M. 1997. "The core domain of the tissue transglutaminase Gh hydrolyzes GTP and ATP". Biochemistry. 36(39):11655-1164.

[41]. Lorand L., Graham R M. 2003. "Transglutaminases: crosslinking enzymes with pleiotropic functions". Nature Reviews Molecular Cell Biology. 4(15):140-156.

[42]. Sarkar N. K., Clarke D. D., Waelsh H. 1957. "An enzymically catalyzed incorporation of amines into proteins". Biochim Biophys Acta 25:451-452.

[43]. Csosz E., Bagossi P., Nagy Z., Dosztanyi Z., Simon, I., & Fesus, L. 2008. "Substrate Preference of Transglutaminase 2 Revealed by Logistic Regression Analysis and Intrinsic Disorder Examination". Journal of Molecular Biology, 383(2), 390-402.

[44]. Facchiano A., Facchiano F. 2009. "Transglutaminases and their substrates in biology and human diseases: 50 years of growing". Amino Acids. 36(9):599-614.

[45]. Lai T. S., Lin C. J., Greenberg C. S. 2017. "Role of tissue transglutaminase-2 (TG2)-mediated aminylation in biological processes". Amino Acids. 49(3):501-515.

[46]. Greenberg C. S., Birckbichler P. J., Rice R. H. 1991. "Transglutaminases: multifunctional cross-linking enzymes that stabilize tissues". The FASEB Journal. 5(15):3071-3077.

[47]. Hasegawa G., Suwa M., Ichikawa Y., Ohtsuka T., Kumagai S., Kikuchi M., Sato Y., Saito Y. 2003. "A novel function of tissuetype transglutaminase: protein disulphide isomerase". Biochem Journal. 373(3):793-803.

[48]. Lai, T. S., Slaughter, T. F., Koropchak, C. M., Haroon, Z. A., & Greenberg, C. S. (1996). C-terminal deletion of human tissue transglutaminase enhances magnesium-dependent GTP/ATPase activity. Journal of Biological Chemistry, 271(49), 31191-31195.

[49]. Porta R., Esposito C., Metafora, S., Malori, A., Pucci, P., Siciliano, R., and Marino, G. 1991. "Mass spectrometric identification of the amino donor and acceptor sites in a transglutaminase protein substrates secreted from the rat seminal vesicles". Bioc.

[50]. Belkin A. M. 2011. "Extracellular TG2: emerging functions and regulation". The FEBS Journal. 278(24): 4704-4716.

[51]. Griffin M., Casadio R., Bergamini C. M. 2002. "Transglutaminases: Nature's biological glues". Biochemical Journa. 2002; 368(2):377-396.

[52]. Telci D., Griffin M. 2006. "Tissue transglutaminase (TG2): a wound response enzyme". Frontiers in Bioscience. 11(1):867-882.

[53]. Nurminskaya M. V., Belkin A. M. 2012. "Cellular functions of tissue transglutaminase". International Review of Cell and Molecular Biology. 294(1):64-97.

[54]. Verderio E. A., Telci D., Okoye A., Melino G., Griffin M., 2003. "A novel RGD independent cell adhesion pathway mediated by fibronectin-bound tissue transglutaminase rescues cells from anoikis." J Biol Chem., 278, 42604-14.

[55]. Fok J. Y., Ekmekcioglu S., Mehta K., 2006. "Implications of tissue transglutaminase expression in malignant melanoma". Mol Cancer Ther., 5, 1493-503.

[56]. Fok J. Y., Mehta K., 2007. "Tissue transglutaminase induces the release of apoptosis inducing factor and results in apoptotic death of pancreatic cancer cells". Apoptosis, 12, 1455-63.

[57]. Fok J. Y., Mehta K., 2007. "Tissue transglutaminase induces the release of apoptosis inducing factor and results in apoptotic death of pancreatic cancer cells". Apoptosis, 12, 1455-63.

[58]. Herman J. F., Mangala L. S., Mehta K., 2006. "Implications of increased tissue transglutaminase (TG2) expression in drug-resistant breast cancer (MCF-7) cells". Oncogene, 25, 3049-58.

[59]. Verma A., Wang H., Manavathi B., Fok J. Y., Mann P. A., Kumar R., Mehta K., 2006. "Increased Expression of Tissue Transglutaminase in Pancreatic Ductal Adenocarcinoma and Its Implications in Drug Resistance and Metastasis." Cancer Res November 1, 66; 10525.

[60]. Erdem M., Erdem, S., Sanli, O., Sak, H., Kilicaslan, I., Sahin, F., & Telci, D. 2014. "Up-regulation of DTG with ITGB1 and SDC4 is important in the development and metastasis of renal cell carcinoma". Urologic Oncology: Seminars and Original Investigation.

[61]. Erdem S., Yegen, G., Telci, D., Yildiz, I., Tefik, T., Issever, H., Sanli, O. 2014. "The increased transglutaminase 2 expression levels during initial tumorigenesis predict increased risk of metastasis and decreased disease-free and cancer-specific surviv.

[62]. Mehta K. 2009. "Tissue transglutaminase expression and drug resistance in ovarian cancer". Expert Review of Obstetrics & Gynecology. 4(2), 105-110.

[63]. Lehmann J. M., Holzmann B., Breitbart E. W., Schmiegelow P., Riethmuller G., Johnson J. P. 1987. "Discrimination between benign and malignant cells of melanocytic lineage by two novel antigens, a glycoprotein with a molecular weight of 113,000 and a protein.

[64]. Ouhtit A., Gaur R. L., Abd Elmageed Z. Y., Fernando A., Thouta R., Trappey A. K., Abdraboh M. E., El Sayyad H. I., Rao P., Raj M. G. 2009. "Towards understanding the mode of action of the multifaceted cell adhesion receptor CD146". Biochimica et Biophysica Acta.

[65]. Noel J. C., Chapron C., Fayt I., Anaf V. 2008. "Lymph node involvement and lymphovascular invasion in deep infiltrating rectosigmoid endometriosis". Fertil Steril; 89:1069-72.

[66]. Ogawa S, Kaku T, Amada S, Kobayashi H, Hirakawa T, Ariyoshi K, Kamura T, Nakano H. 2000. "Ovarian endometriosis associated with ovarian cancer: a clinicopathological and immunohistochemical study". Gynecol Oncol; 77: 298-304.

[67]. Modesitt S C, Tortolero-Luna G, Robinson J B, Gershenson D M, Wolf J. K., 2002. "Ovarian and extraovarian endometriosis associated cancer". Obstet Gynecol 100:788-95.

[68]. Bertelsen L, Mellemkjær L, Frederiksen K, Kjær S K, Brinton L A, Sakoda L C, van Valkengoed I, Olsen J H. 2006. "Risk for breast cancer among women with endometriosis". Int J Cancer; 120:1372-75.

[69]. Wang Y, Qiu H, Hu W, Li S, Yu J. 2014. "Overexpression of platelet-derived growth factor-D promotes tumor growth and invasion in endometrial cancer." Int J Mol Sci. 15(3):4780-4794.

[70]. Fredriksson L., Li H., Eriksson U. 2004. "The PDGF family: Four gene products form five dimeric isoforms". Cytokine Growth Factor Rev. 15:197-204.

[71]. Yu J., Ustach C., Kim H. R. 2003. "Platelet-derived growth factor signaling and human cancer". J. Biochem. Mol. Biol. 36:49-59.

[72]. Wang Z., Kong D., Li Y., Sarkar F. H. 2009. "PDGF-D signaling: A novel target in cancer therapy. Curr. Drug Targets". 10:38-41.

[73]. Gargett C. E., Schwab K. E., and Deane J. A., (2016 (a)). "Endometrial stem/progenitor cells: the first 10 years". Hum Reprod Update. March; 22(2): 137-163.

[74]. Gargett C. E., Gurung S. (2016(b)). "Endometrial Mesenchymal Stem/Stromal Cells, Their Fibroblast Progeny in Endometriosis, and More" Biology of Reproduction, Volume 94, Issue 6, 1 June 129, 1-4.

[75]. Barragan F, Irwin J C, Balayan S, Erikson D W, Chen J C, Houshdaran S, Piltonen T T, Spitzer T, George A, Rabban J T, Nezhat C, Giudice L C. 2016. "Human endometrial fibroblasts derived from mesenchymal progenitors inherit progesterone resistance and acquire an Inflammatory Phenotype in the Endometrial Niche in Endometriosis" Biology of Reproduction, Volume 94, Issue 5, 1 May 118, 1-20.

[76]. Nayman A. H., Siginc H., Zemheri E., Yencilek F., Yildirim A., Telci D. 2019. "Dual-Inhibition of mTOR and Bcl-2 Enhances the Anti-tumor Effect of Everolimus against Renal Cell Carcinoma In Vitro and In Vivo". J Cancer. 10(6):1466-1478.

[77]. Peskin A. V., Winterbourn C. C. 2000. "A microtiter plate assay for superoxide dismutase using a water-soluble tetrazolium salt (WST-1)". Clin Chim Acta. 293 (1-2):157-66.

[78]. Samani E. N., Mamillapalli R., Li F. 2017. "Micrometastasis of endometriosis to distant organs in a murine model". Oncotarget. 10(23):2282-2291.

[79]. Gao X., Outley J., Botteman M. 2006. "Economic burden of endometriosis". Fertil Steril. 86:1561-72.

[80]. Mishra V. V., Gaddagi R. A., Aggarwal R., Choudhary S., Sharma U., Patel U. 2015. "Prevalence; Characteristics and Management of Endometriosis Amongst Infertile Women: A One Year Retrospective Study". J Clin Diagn Res. 9(6): QC01-QC3.

[81]. Eisenberg V. H., Weil C., Chodick G., Shalev V. 2018. "Epidemiology of endometriosis: a large population-based database study from a healthcare provider with 2 million members". BJOG. 125(1):55-62. doi:10.1111/1471-0528.14711.

[82]. Soliman A. M., Surrey E., Bonafede M., Nelson J. K., Castelli-Haley J. 2010. "Real-World Evaluation of Direct and Indirect Economic Burden Among Endometriosis Patients in the United States". Adv Ther. 35(3):408-423.

[83]. Wang P. H., Lee W. L., Yuan C. C. 2001. "Major complications of operative and diagnostic laparoscopy for gynecologic disease". J Am Assoc Gynecol Laparosc. 8(1):68-73.

[84]. Weintraub A. Y., Soriano D., Seidman D. S., Goldenberg M., Eisenberg V. H., 2014. "Think Endometriosis: Delay in Diagnosis or Delay in Referral to Adequate Treatment?". Journal of Fertilization: In Vitro—IVF—Worldwide, Reproductive Medicine, Genetics & Stem.

[85]. Hirsch M., Davis C. J. 2015. "Preoperative assessment and diagnosis of endometriosis". Current Opinion in Obstetrics and Gynecology, 27(4), 284-290.

[86]. Chan R. W., Schwab K. E., Gargett E. C., 2004. "Clonogenicity of Human Endometrial Epithelial and Stromal Cells". Biology of Reproduction 70, 1738-1750.

[87]. Dominici M, Le Blanc K, Mueller I, Slaper-Cortenbach I, Marini F, Krause D, Deans R, Keating A, Prockop Dj, Horwitz E. 2006. "Minimal criteria for defining multipotent mesenchymal stromal cells". The International Society for Cellular Therapy position sta.

[88]. Meng X, Ichim T E, Zhong J, Rogers A, Yin Z, Jackson J, Wang H, Ge W, Bogin V, Chan K W, Thébaud B, Riordan N H. 2007. "Endometrial regenerative cells: a novel stem cell population". J Transl Med. 15; 5:57.

[89]. Masuda, H., Maruyama, T., Gargett, C. E., Miyazaki, K., Matsuzaki, Y., Okano, H., & Tanaka, M. 2015. "Endometrial Side Population Cells: Potential Adult Stem/Progenitor Cells in Endometrium". Biology of Reproduction, 93(4).

[90]. Gargett, C. E. 2006. "Identification and characterisation of human endometrial stem/progenitor cells". The Australian and New Zealand Journal of Obstetrics and Gynaecology, 46(3), 250-253.

[91]. Gargett, C. E., & Ye, L. 2012. "Endometrial reconstruction from stem cells". Fertility and Sterility, 98(1), 11-20.

[92]. Schwab K. E., Gargett C. E. 2007. "Co-expression of two perivascular cell markers isolates mesenchymal stem-like cells from human endometrium". Human Reproductive. 22(11):2903-2911.

[93]. Zemskov E A, Loukinova E, Mikhailenko I, Coleman R A, Strickland D K, Belkin A M. Regulation of platelet-derived growth factor receptor function by integrin-associated cell surface transglutaminase. Journal of Biological Chemistry. 2009; 284(24):16693-16703.

[94]. Zemskov E. A., Mikhailenko I., Smith E. P, Belkin A. M. 2012. "Tissue transglutaminase promotes PDGF/PDGFR-mediated signaling and responses in vascular smooth muscle cells". Journal of Cellular Physiology, 227(5), 2089-2096.

[95]. Chen J., Luo Y., Huang H. 2018. "CD146 is essential for PDGFRβ-induced pericyte recruitment". Protein Cell. 9(8):743-747.

[96]. Moore C. B., Guthrie E. H., Huang M. T., Taxman D. J. 2010. "Short hairpin RNA (shRNA): design, delivery, and assessment of gene knockdown". Methods Mol Biol; 629:141-58.

[97]. Folk J. E. 1983. "Mechanism and basis for specificity of transglutaminase-catalyzed epsilon-(gamma-glutamyl) lysine bond formation". Adv Enzymol Relat Areas Mol Biol. 54:1-56.

[98]. de Macédo P., Marrano C., Keillor J. W. 2000. "A direct continuous spectrophotometric assay for transglutaminase activity". Anal Biochem. 1; 285(1):16-20.

[99]. Iismaa S. E., Mearns B. M., Lorand L., Graham R. M. 2009. "Transglutaminases and disease: lessons from genetically engineered mouse models and inherited disorders". Physiol Rev 89:991-1023.

What is claimed is:

1. A diagnostic kit for detecting endometriosis in a human subject, comprising:

(a) at least one reagent for detecting tissue transglutaminase (tTG) mRNA expression, tTG protein expression, or both; and (b) at least one reagent for detecting at least one biomarker selected from the group consisting of cluster of differentiation 146 (CD146), sushi domain containing protein 2 (SUSD2), integrin beta 1 (ITGB1), and platelet derived growth factor receptor (PDGFR);

wherein the diagnostic kit is configured to measure an expression level of the tTG and the at least one biomarker in mesenchymal stem cells isolated from eutopic endometrial tissue and/or menstrual blood.

2. The diagnostic kit of claim 1, wherein an expression level of the tTG and the at least one biomarker, each relative to its corresponding reference level, is indicative of endometriosis.

3. The diagnostic kit of claim 1, wherein the reagent for detecting tTG comprises an antibody.

4. The diagnostic kit of claim 1, wherein the reagent for detecting tTG comprises at least one nucleic acid probe or primer.

5. The diagnostic kit of claim 1, wherein the kit is configured for multiplex detection.

6. A method of evaluating a response to treatment in a human subject having endometriosis, comprising:

(a) isolating mesenchymal stem cells from eutopic endometrial tissue and/or menstrual blood obtained from the subject at a first time point before a drug treatment and at a second time point after the drug treatment;

(b) quantifying tissue transglutaminase (tTG) mRNA and/or protein expression and expression of at least one biomarker selected from CD146, SUSD2, ITGB1, and PDGFR in the isolated mesenchymal stem cells;

(c) comparing expression levels between the first and second time points; and (d) determining a response to treatment based on a change in expression levels, wherein the quantification is optionally performed using the diagnostic kit of claim 1.

7. The method of claim 6, wherein the expression level of the tTG mRNA is at least 2.5-fold higher than the reference level.

8. The method of claim 6, wherein the expression level of the tTG protein is at least 4-fold higher than the reference level.

9. The method of claim 6, wherein the expression level of the tTG and the at least one biomarker are each increased relative to the corresponding reference levels, and wherein the combined increase is indicative of endometriosis.

10. The method of claim 6, wherein a reduction of the expression level of the tTG results in a corresponding decrease in the expression of the at least one biomarker.

* * * * *